United States Patent
Godfrey et al.

(10) Patent No.: US 7,980,149 B2
(45) Date of Patent: Jul. 19, 2011

(54) DOCKING MECHANISM FOR A SENSOR CARTRIDGE

(75) Inventors: Daniel Peterson Godfrey, Cambridge (GB); Mark John Frogley, Huntington (GB); Christopher Durham Whalen, Pleasant Prairie, WI (US)

(73) Assignee: Inverness Medical Switzerland GmbH, Zug (CH)

( * ) Notice: Subject to any disclaimer, the term of this patent is extended or adjusted under 35 U.S.C. 154(b) by 705 days.

(21) Appl. No.: 11/817,853

(22) PCT Filed: Mar. 31, 2006

(86) PCT No.: PCT/GB2006/001164
§ 371 (c)(1),
(2), (4) Date: Apr. 25, 2008

(87) PCT Pub. No.: WO2006/103440
PCT Pub. Date: Oct. 5, 2006

(65) Prior Publication Data
US 2009/0114044 A1  May 7, 2009

(30) Foreign Application Priority Data

Apr. 1, 2005 (GB) .................................. 0506711.1
Jul. 30, 2005 (GB) .................................. 0515757.3

(51) Int. Cl.
B01L 99/00 (2010.01)
B01L 9/00 (2010.01)
G01N 27/00 (2006.01)

(52) U.S. Cl. .................. 73/864.85; 73/65.56; 422/544; 422/554

(58) Field of Classification Search ................. 73/64.56, 73/864.81, 864.85, 864.91; 422/103–104
See application file for complete search history.

(56) References Cited

U.S. PATENT DOCUMENTS

| 6,196,059 B1 * | 3/2001 | Kosslinger et al. .......... 73/61.49 |
| 6,990,852 B2 | 1/2006 | Berndt |
| 7,093,482 B2 | 8/2006 | Berndt |
| 7,811,523 B2 * | 10/2010 | Bjornson et al. .............. 422/104 |
| 2006/0141608 A1 * | 6/2006 | Aastrup et al. ............. 435/287.1 |
| 2009/0061450 A1 * | 3/2009 | Hunter ............................... 435/6 |

FOREIGN PATENT DOCUMENTS

| WO | WO-02/12873 A2 | 2/2002 |
| WO | WO-2004/022233 A1 | 3/2004 |
| WO | WO-2004/057319 A1 | 7/2004 |
| WO | WO 2010088514 A1 * | 8/2010 |

* cited by examiner

Primary Examiner — Thomas P Noland
(74) Attorney, Agent, or Firm — Barnes & Thornburg LLP

(57) ABSTRACT

A docking mechanism provided for analytical apparatus, such as an acoustic bio-sensor apparatus. The mechanism is operable releasably to receive a cartridge (58) for use in analysing a sample comprising a fluid and having a flow cell (104, 106; 304, 306) for the sample and an electrically operated sensor (92) for performing the analysis. The docking mechanism has a clamping mechanism (12, 8, 10) for urging a fluid connector such as ferules (50, 52) against the cartridge to provide a fluid connection between the flow cell inlet and a sample delivery device. The docking mechanism also has an electrical connector (74, 76, 78) for engaging the sensor to connect the latter to electrical circuitry for operating the sensor, the electrical connector being moveable towards and away from the sensor relative to the clamping mechanism, so that, in use, the electrical connector exerts on the sensor a force which is sufficient to maintain the necessary electrical connection, while not being so great as to have a substantial detrimental effect on the accuracy of the sensor. There is also shown analytical apparatus which includes such a docking mechanism.

29 Claims, 19 Drawing Sheets

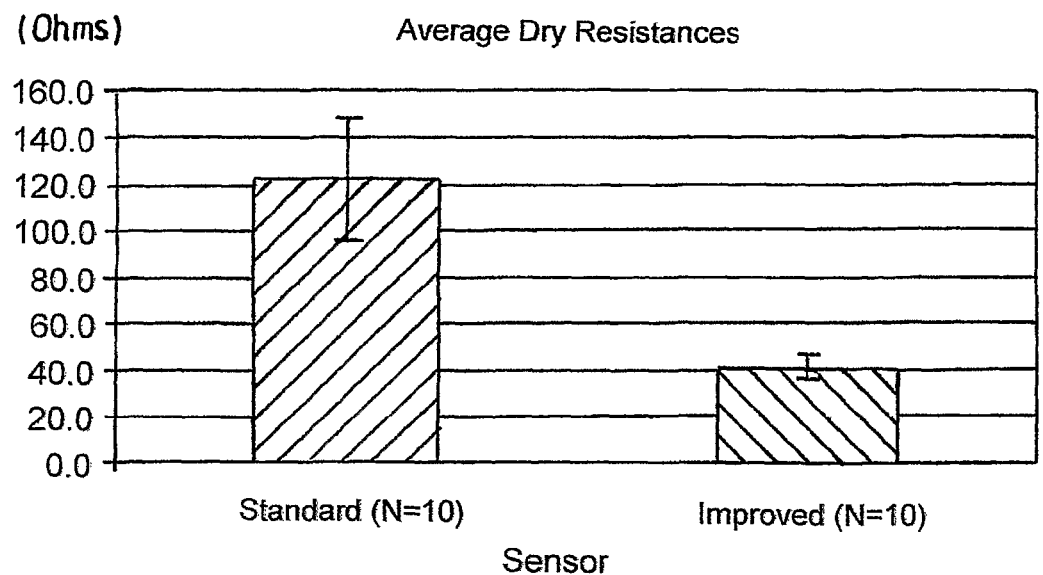
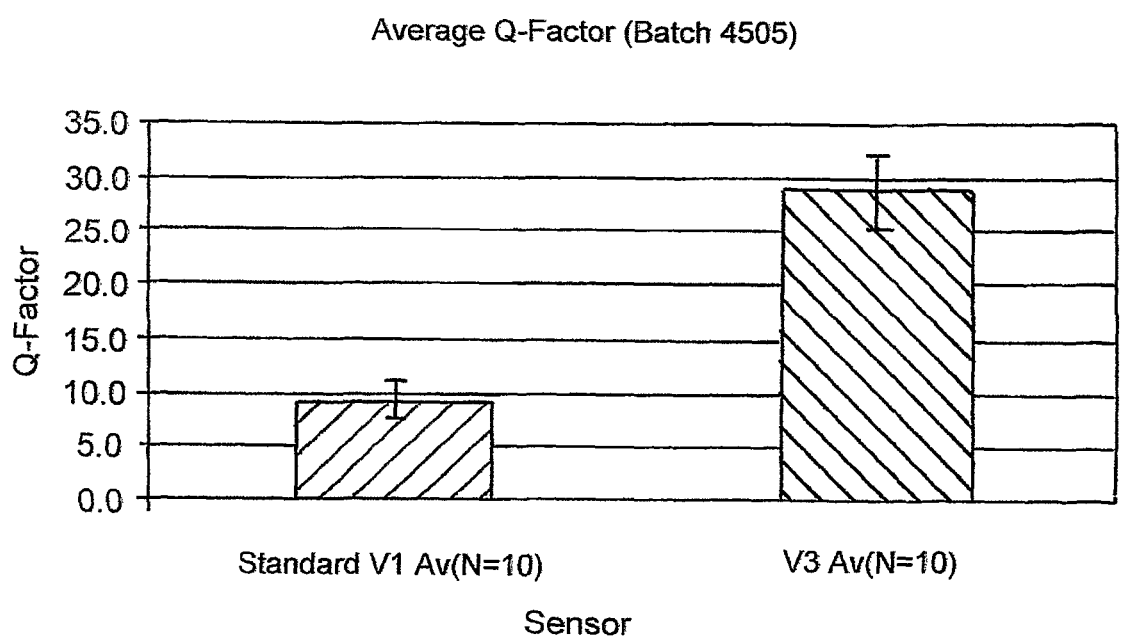
Fig. 23

DOCKING MECHANISM FOR A SENSOR CARTRIDGE

STATEMENT REGARDING FEDERALLY SPONSORED RESEARCH OR DEVELOPMENT

This invention is made with US Government support under Grant No: 5U01AI061243-05 awarded by USAMRIID and NIAID. The Government has certain rights in the invention.

FIELD OF THE INVENTION

This invention relates to a docking mechanism for releasably receiving a cartridge for use in analysing a sample comprising fluid, and to analysing apparatus which includes such a docking mechanism and cartridge.

BACKGROUND TO THE INVENTION

The invention is particularly, but not exclusively, applicable to apparatus, for example a quartz crystal microbalance system, which uses an electrical-mechanical transducer as a sensor. In such a system, an electrical signal causes the transducer to vibrate.

The crystal typically has an active surface on which a receptor group is immobilised. That group has a chemical affinity or reactivity towards a substance to be detected or analysed. The substance to be analysed is normally present in a fluid which is bought into contact with the active surface of the crystal. Physical, chemical and biochemical interactions between the receptor group on the active surface and the substance cause a change in the mass attached to the surface (and in other physical properties of the active surface) and these affect the vibrational characteristics, in particular the resonant frequency, of the crystal. Analysis of these effects can be used to obtain qualitative and/or quantitative data on the substance, and its interaction with the receptor.

This type of analysing apparatus is used in situations, for example to analyse chemical and biochemical interactions, in which it may be desirable to interchange the sensor with another sensor which may be identical to the first sensor or may carry a different receptor group. To that end, it is known to provide the sensor and a flow cell, for bringing the sample into contact with the sensor, in a cartridge which co-operates with a docking mechanism in the analysing apparatus in order to releasably connect inlet and outlet openings for the flow cell to a sample delivery/removal system. The docking mechanism also connects the electrodes on the sensor to diving/measuring circuitry for oscillating the sensor and measuring the frequency of oscillation and/or other characteristics of the oscillation (for example the magnitude of the damping force being experienced by the sensor).

U.S. Pat. No. 6,196,059 shows an example of such apparatus. The cartridge comprises an injection moulded body which has an annular rib that surrounds a surface that is to fort the base of the flow cell and that includes inlet and outlet openings which communicate with an inlet and outlet of the cartridge through small tubes. The sensor is adhered to the rib which spaces the sensor from the other surface so that the sensor, the surface and the rib between them define the flow cell. The cartridge is received in a docking mechanism that comprises a lid pivotally mounted on a base. The base includes fluid conduits for connecting the inlet and outlet ribs of the cartridge to a sample delivery/removal system, whilst the lid of the mechanism includes an electrical connector for connecting the electrodes of the sensor to the drive/measurement circuitry. Although the connector is described as being spring loaded, it appears to exert enough force on the cartridge to require that the connector engages contacts which are laterally spaced from the sensor so that the electrical connector does not exert a force directly on the sensor. As a result, the cartridge is of a relatively complicated construction having two spaced apart contacts for the electrical connector and wires connecting those contacts to the electrodes on the sensor.

SUMMARY OF THE INVENTION

According to a first aspect of the invention, there is provided a docking mechanism for releasably receiving a cartridge for use in analysing a sample comprising a fluid, the cartridge having a flow cell for the sample and an electrically operated sensor for performing said analysis, the docking mechanism comprising a clamping mechanism for urging fluid connector means against the cartridge to provide a fluid connection between the flow cell inlet and sample delivery means; the docking mechanism also comprising an electrical connector for engaging the sensor to connect the latter to electrical circuitry for operating the sensor, the electrical connector being movable, towards and away from the sensor, relative to the clamping mechanism, so that, in use, the electrical connector exerts on the sensor a force which is sufficient to maintain the necessary electrical connection, whilst not being so great as to have a substantial affect on the accuracy of the sensor.

Thus the invention enables the fluid connector to be urged against the cartridge with sufficient force to create a seal with the cartridge, without causing the electrical connector to exert too great a force on the sensor.

Preferably, the clamping mechanism comprises a carrier member and a co-operating surface, at least one of which is movable towards and away from the other, releasably to compress a cartridge therebetween.

In one embodiment of the invention, the carrier member is attached to a fixed reference surface, and the co-operating surface is movable. In another embodiment, the co-operating surface constitutes the fixed reference surface which locates the cartridge in position in the mechanism, so that the movable member is the carrier member.

Preferably, the carrier member carries the fluid connector means.

Preferably, the fluid connector means comprises a connector so sized and shaped as to make mating engagement with a complimentary connector on a cartridge.

In this case, the fluid connector means of the docking mechanism may conveniently be the male connector.

This enables the cartridge to have a recessed female connector, and thus to be of a relatively compact construction.

Preferably, the male fluid connector comprises a tube which is, in use, inserted into a bore in a cartridge received in the docking mechanism. The tube is preferably a ferrule.

The fluid connector on the carrier member may to advantage be one of two such connectors for respective connection to an inlet and an outlet of a flow cell of a cartridge.

The docking mechanism may to advantage include actuation means for automatically closing and opening the clamping mechanism, respectively to clamp and release the cartridge.

Preferably, the actuation means also acts on the electrical connector automatically to move the connector into and out of engagement with the sensor.

The carrier member and electrical connector may conveniently be arranged in an opposed relationship so that a cartridge received in the docking mechanism is interposed between the carrier member and the electrical connector.

Thus the fluid and electrical connections for the sensor are made from opposite sides of the cartridge, so that the cartridge can be of a relatively compact and simple construction.

In this case, the actuation means preferably comprises a drive assembly which acts between the electrical connector and the carrier member to alter the separation therebetween.

Where the co-operating surface is interposed between the carrier member and electrical connector, the drive assembly is preferably fixed in position relative to the co-operating surface.

This allows a single drive assembly to be used to bring both the electrical and fluid connectors into and out of engagement with the cartridge, and for the fluid connector to be urged against the cartridge with a greater force than the electrical connectors.

The drive assembly conveniently comprises a hydraulic or pneumatic gas cylinder. Alternatively, the drive assembly includes a motor for driving the electrical connector and carrier member.

The actuation means is preferably operable to close the clamping mechanism before bringing the electrical connector into engagement with a sensor.

The clamping mechanism preferably includes a clamping mechanism biasing means for urging the clamping mechanism into a closed position.

Preferably the docking mechanism includes electrical connector biasing means, weaker than said clamping mechanism biasing means, for urging the electrical connector into engagement with the sensor of a cartridge in the docking mechanism.

Where the clamping mechanism includes said drive assembly, the clamping mechanism and electrical connector biasing means may form part of the actuating mechanism.

With this arrangement, the drive assembly is operable only to separate the carrier member and electrical connector from the cartridge, the force with which those components engage the cartridge being determined by the clamping mechanism biasing means and electrical connector biasing means.

Thus the drive assembly operates to release a cartridge from the docking mechanism. When a fresh cartridge is inserted, the drive assembly is then deactivated so that it ceases to counteract the effect of the two biasing means. As a result, the clamping mechanism biasing means first urges the carrier member towards the cartridge whilst acting on the electrical connector at least through the driver assembly to prevent the latter from moving towards the cartridge until the cartridge has been engaged by the carrier member. Once this happens, the electrical connector biasing means moves the electrical connector into contact with the sensor.

Preferably, the electrical connector is mounted on a further carrier member movable relative to cartridge in the docking mechanism to bring the electrical connector into and out of engagement with the sensor.

Preferably, the electrical connector biasing means acts on said further carrier member.

The electrical connector may to advantage be one of two such connectors, each for connecting a respective electrode of the sensor to the circuitry.

Preferably, the or each electrical connector comprises a spring loaded pin.

Preferably, the co-operating surface is so arranged as to engage the cartridge to retain the latter in position in the docking station.

To that end, the co-operating surface may comprise a formation, for example a rib or groove, which is fixed relative to the docking mechanism and which receives an edge portion of a cartridge.

Said formation may conveniently form part of, or be attached to, a frame of the docking mechanism.

Preferably, the further carrier member comprises a printed circuit board which may to advantage include interface circuitry for matching the sensor to the circuitry for operating the latter.

For example, the printed board may carry switching and/or impedance matching circuitry.

With this arrangement, analytical apparatus equipped with this sort of docking station may be relatively easily modified, by interchanging the printed circuit board with another printed circuit board having interface circuitry of differing characteristics, to be compatible with different types of sensor.

If the docking mechanism is operable to receive the plurality of cartridges simultaneously, the PCB may additionally include switching circuitry to enable each cartridge in turn to be connected to the circuitry for operating the sensors.

According to a second aspect of the invention, there is provided a docking mechanism for releasably receiving a cartridge for use in analysing a sample comprising a fluid, the cartridge having a sensor for performing said analysis, the docking mechanism comprising opposed first and second carrier members movable in use towards and away from the position to be occupied by a cartridge in the mechanism, and co-operating means for locating the cartridge between the carrier members, the first carrier member carrying a fluid connector for making a fluid connection between the cartridge and a sample delivery means, the second carrier member carrying an electrical connector for connecting the sensor to circuitry for operating the latter, wherein the co-operating surface prevents movement of a cartridge, received by the docking mechanism, in the directions of movement of the carrier members.

Thus the force applied to the cartridge by the first carrier member clamps the cartridge against the locations without transmitting any substantial amount of force to the second carrier member or electrical connector.

Preferably, the location means comprises a co-operating surface, such as a rib or groove against which the periphery a cartridge in the docking mechanism is seated.

The invention also lies in analysing apparatus for analysing samples comprises a fluid, the apparatus comprising a cartridge having an electrically operated sensor for analysing the sample, a docking mechanism and hereinabove described, for releasably receiving the cartridge, sample delivery means for delivering the sample, via the docking mechanism to the cartridge and electrical circuitry for operating the sensor.

Preferably, the cartridge contains a flow cell for bringing the sample into contact with the sensor.

Preferably, the sensor comprises an electrical-mechanical transducer, for example a piezoelectric, piezomagnetic or acoustic transducer. One example of such a sensor is a quartz crystal microbalance. Other suitable transducers include surface acoustic wave devices, Love wave devices etc.

The transducers may be provided either in single cartridges, cartridges containing multiple transducers, or as multiple cartridges, either in linear (e.g. 1×4) or array configuration (e.g. 4×4), or combinations of these two arrangements.

The cartridge may be provided with further apertures through which during the electronic clamping action earthed pins pass. These earthed pins are earthed by contact with an earth rail on the circuit board, and on completion of the clamping action contact an earthed bar of the structure. The function of these earthed bars is to form a "Faraday cage" around the drive pins and electrodes of the sensor. By suitable election of the separation of these earth pins, a means of suppressing the emission of RF signals from the transducer and drive pins can be engaged automatically on closing the clamping action.

Additionally or alternatively, these pins may locate the cartridge in position in the mechanism.

BRIEF DESCRIPTION OF THE DRAWINGS

The invention will now be described, by way of example only, with reference to the accompanying drawings, in which:

FIG. 23 compares, graphically, the resistance and Q-Factor of the modified version with the version of sensor shown in FIGS. 10 and 17 to 19;

DETAILED DESCRIPTION

Figure 1:
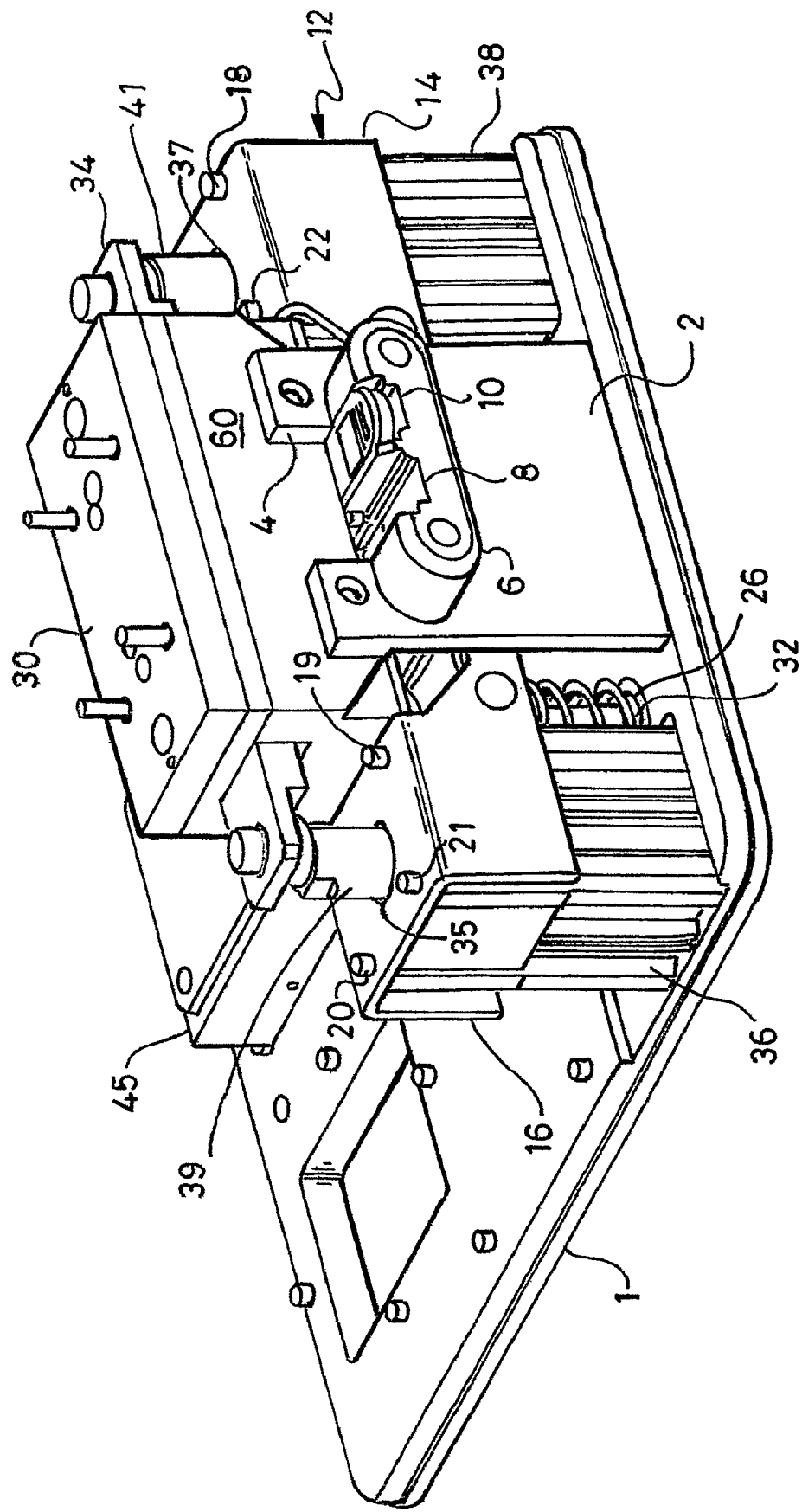
FIG. 1 is an isometric view of a first embodiment of a docking mechanism, in accordance with the invention, for an analyser, also in accordance with the invention, the mechanism being shown with one cartridge inserted therein, and with its clamping mechanism in its open condition.

With reference to FIG. 1, a docking mechanism comprises a base plate 1 from which a front plate 2 rises vertically. At the top of the front plate 2 there is provided a vertical generally U-shaped slot 4 at the base of which a cartridge location bar 6 is provided. The bar 6 extends horizontally across the bottom of the slot 4, and is secured to the plate by means of bolts or rivets at either side of the slot 4. The top of the bar 6 is provided with a pair of parallel horizontal channels 8 and 10. These channels (8 and 10) have opposed side slots in which cartridges containing the flow cells and sensors for use in the analysis are located. Thus the bar 6 co-operates with the base plate 2 and front plate 4 to fix the vertical position of the cartridges during the use of the docking station.

Situated immediately behind the front plate 2 is a carrier member 12 which has two U-sectioned end portions 14 and 16, each of which includes a set of four apertures into each of which a respective bolt extends. Five of those bolts are visible in FIG. 1, and are denoted by reference numerals 18-22. The bolts extend vertically upwards from the base of actuators 36 and 38 such as hydraulic or pneumatic cylinders, to the underside of the carrier member 12. In between the two end portions 14 and 16, there is a plate (which will be described in more detail in relation to FIGS. 3-8), which bears fluidic connections for connecting flow cells in the cartridges to a sample delivery/removal system (also described below).

The carrier member 12 is also slideably mounted on two support and guide posts, one of which is shown at 26, which extend vertically upwards from the plate 1 to an upper plate 30 to support the latter in position in the mechanism. Each of the support posts includes a carrier member biasing means in the form of a respective compression spring such as the spring 32. The other post is shown at 40 in FIG. 4.

The frame of the machine comprises base plate 1, the front plate 2 and the upper plate 30. A further carrier member in the form of plate 34 is situated immediately beneath the plate 30 and includes apertures through which the support and guide posts extend so that the upper carrier plate can move vertically relative to the machine frame. The carrier member 12 includes apertures 35 and 37 through which the push rods of the actuating cylinders extend (see FIG. 3). The tops of these rods act against the underside of the plate 34. The upper plate 30 is attached to the instrument frame and provides a reference surface. All plates, carriers the machine frame and the like are constructed of aluminium unless otherwise specified.

The push rods of the cylinders are denoted by reference numerals 39 and 41, and constructed of stainless steel. As can be seen from FIG. 3, the support and guide post 26 and corresponding vertical support post 40 (the associated compression spring for which is shown at 42) flank plate portion 44 of the lower carrier member 12. That portion is provided in its upper face with a U-shaped channel 46 which accommodates a microfluidic manifold 48 forming part of the fluid supply/removal system. The manifold is a microfluidic system for storing, switching and delivering fluids to the cartridge, and is of a general type known from existing instrumentation, and the rest of the system is shown at 45. For example the manifold may comprise a first channel for retaining and supplying samples to the cartridge (under control of an inlet valve) and a further channel for receiving used samples from the cartridge. The manifold 48 communicates with inlet ferrule connectors 50 and 52. Each of these connectors is aligned with a respective female connector, (54 and 56) in a cartridge 58 (held in channel 8), so as to enable fluid to be supplied to each of two flow cells in the cartridge 58. The manifold also includes two outlet ferrule connectors (not shown) aligned, in use with outlet connectors (not shown) on the cartridge.

For one or more examples of how ferrules may be used to connect microfluidic systems, reference is made to WO2004/022233 (Epigem).

The cartridge 58, when received in the docking mechanism, is located by a channel in the bar 6 and by means of a cartridge mounting block 60. The cartridge mounting block 60 includes passages 62 and 64 through each of which a respective one of the posts 26 and 40 extends. Unlike the plates 34 and 44, however, the block 60 is fixed to these posts and is thus supported in a fixed vertical position relative to the base plate 1. The block 60 includes a slot 66 in its lower surface which is of a substantially T-shaped cross section corresponding to the cross sectional shape of the cartridge 58 so that the cartridge 58 may be slid into and out of the slot 66. The upper surface of the block 60 includes three vertical bores, 68, 70 and 72 which extend from the top of the block to the slot 66 and which accommodate corresponding electrical connectors in the form of vertical spring loaded gold plated contact pins 74, 76 and 78 which extend vertically down from a printed circuit board 80 carried on the underside of the upper carrier plate 34. In the present example the contact pins 74, 76 and 78 are coda pins, although other types of spring loaded gold plated contact pins may be used.

Figure 4:
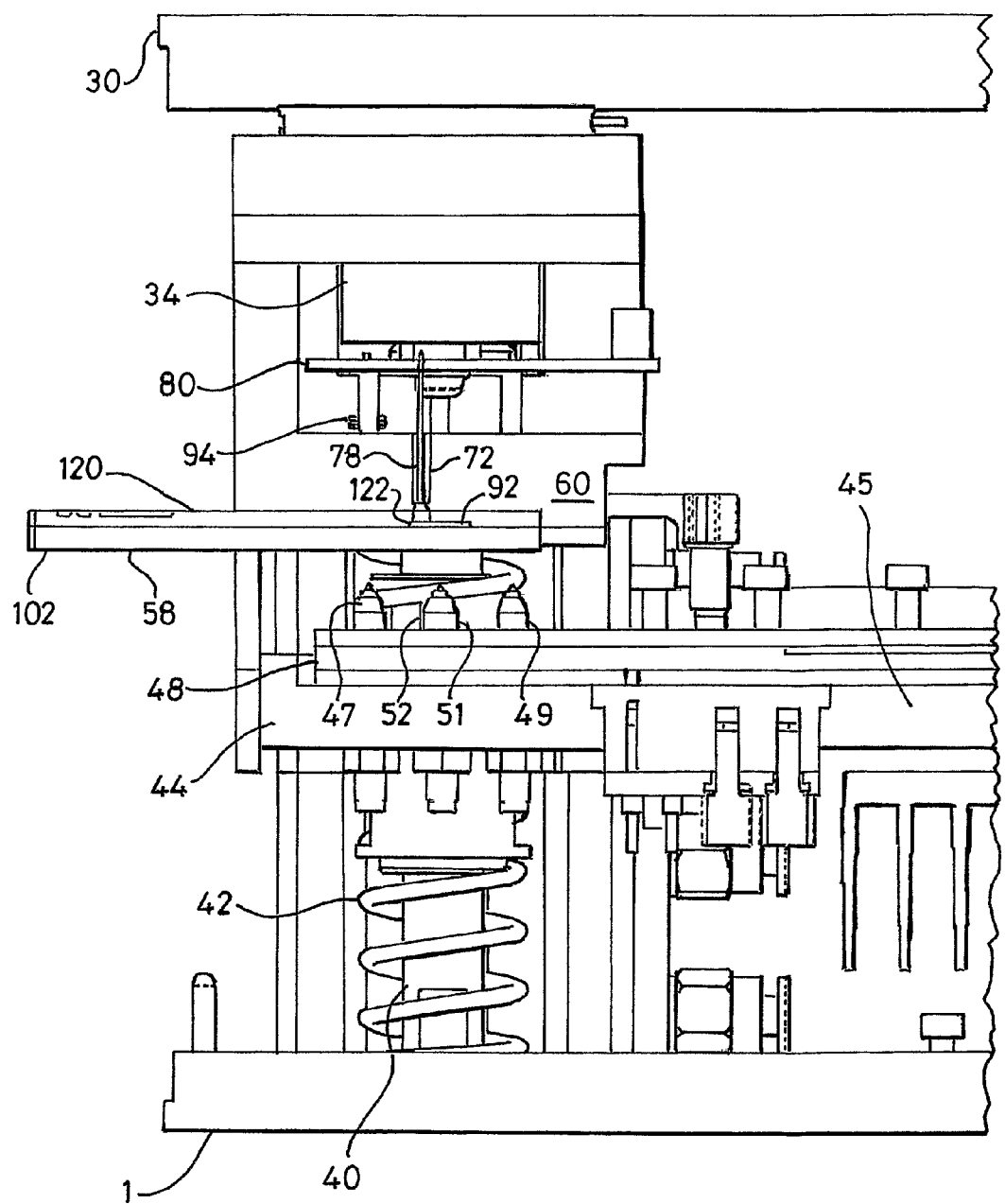
FIG. 4-6 are sectional side views of part of the docking mechanism of FIGS. 1 and 2 at successive stages during the operation of the mechanism.
Figure 5:
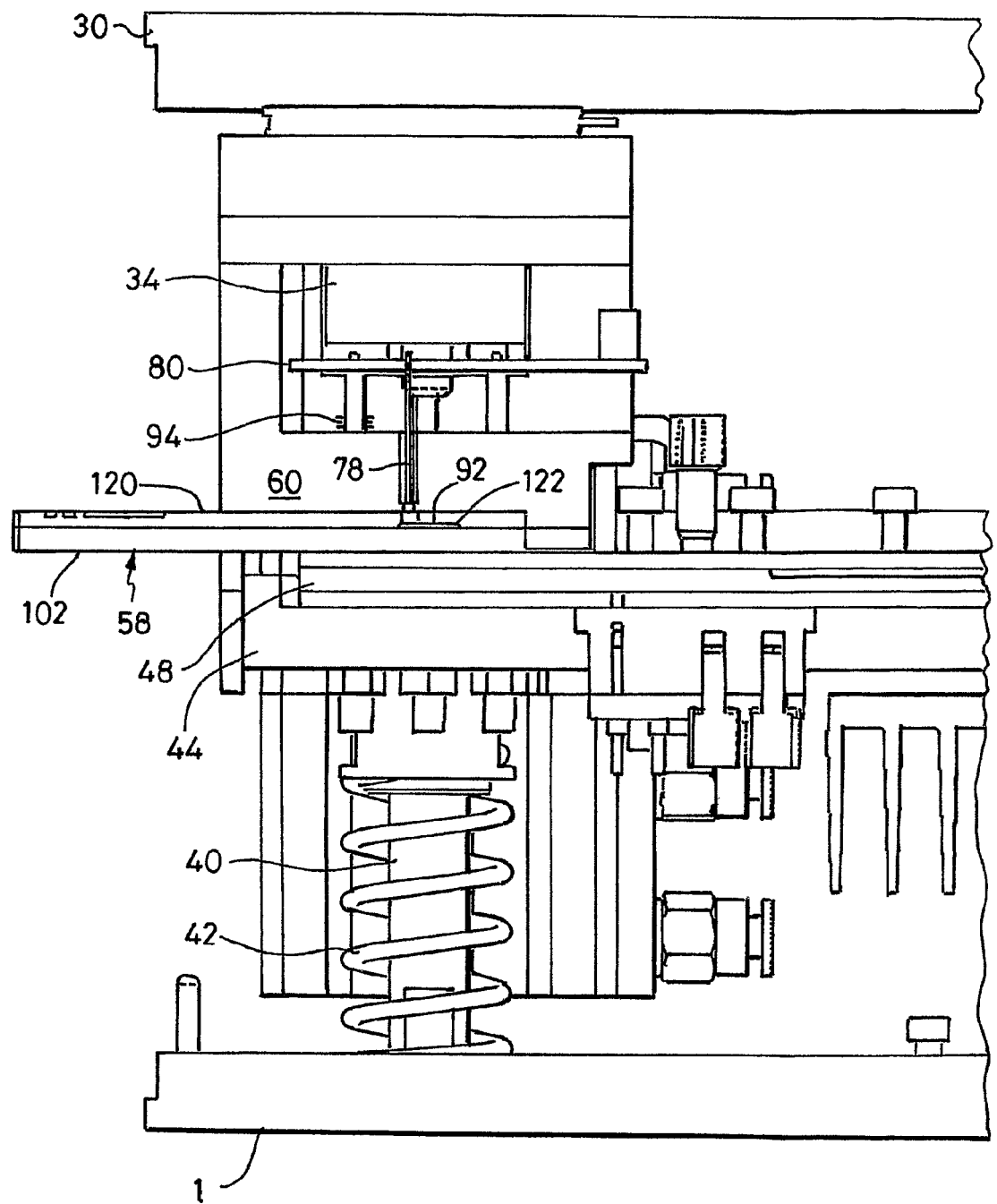
Figure 14:
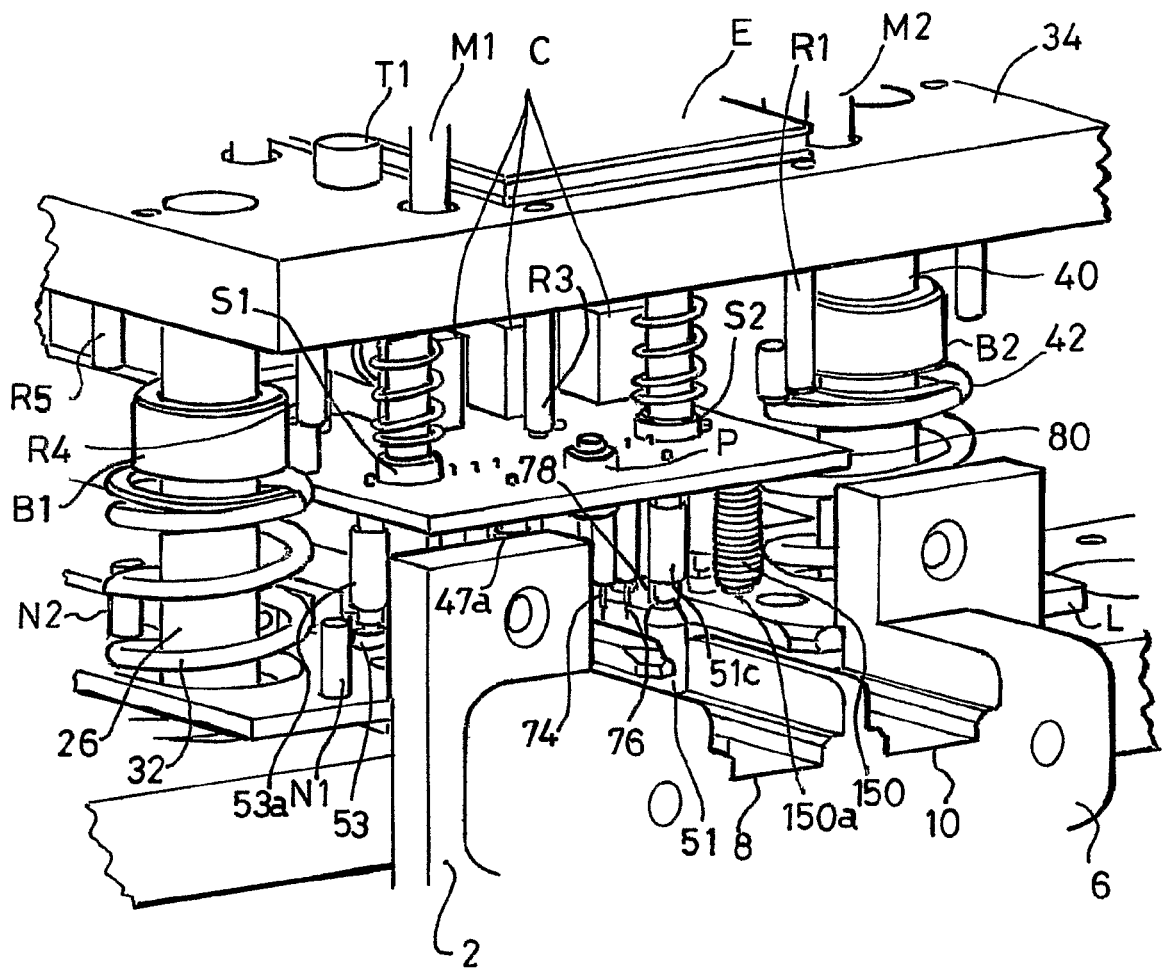
FIG. 14 is a more detailed view of part of the apparatus shown in FIG. 13.

With reference to FIG. 4, the plate 44 also carries a set of earthed, electrically conductive vertical location pins, three of which are denoted by numerals 47, 49 and 51, the view of the fourth being blocked by pin 51 (but the corresponding pin is shown at 53 in FIG. 14). In use, the pins 47 and 49 extend through apertures in the cartridge while the remaining two pins engage opposite sides of the cartridge. These four pins further locate the cartridge in the docking mechanism, and also form a Faraday cage around the flow cell in the cartridge. To that end each pin engages a respective opposed downwardly directed pin which is mounted on the circuit board, and connected to the earth rail of the latter, so that the pins form an earthed cage.

The upper pins are not visible in the sectional side views (and have been omitted from FIGS. 3, 7 and 8) for the sake of clarity. However, in the embodiment shown in FIGS. 13 and 14, one of the pins is shown at 51a. Another upper earth pin 53a and opposed pin 53 are also shown in FIG. 14. The pin 53 engages the opposite side of the cartridge from the pin 51.

It will be appreciated that the springs 32 and 42 constitute the clamping mechanism biasing means.

The plate 34, and hence the PCB 80 and coda pins, is biased in the downward direction by a pair of compression springs 82 and 84 which function as electrical connector biasing means for the apparatus. Each of the springs 82 and 84 is located on a respective one of two vertical spring location rods 86 and 87 mounted on the plate 34.

The PCB 80 carries impedance matching and switching circuitry which enables drive/measurement circuitry to operate the sensor in the cartridge 58. In this particular example, the drive/measurement circuitry comprises an oscillator circuit with automatic gain control means such as is described in the present Applicant's UK Patent No. GB 0413134.8 or that in WO00/25118.

Figure 7:
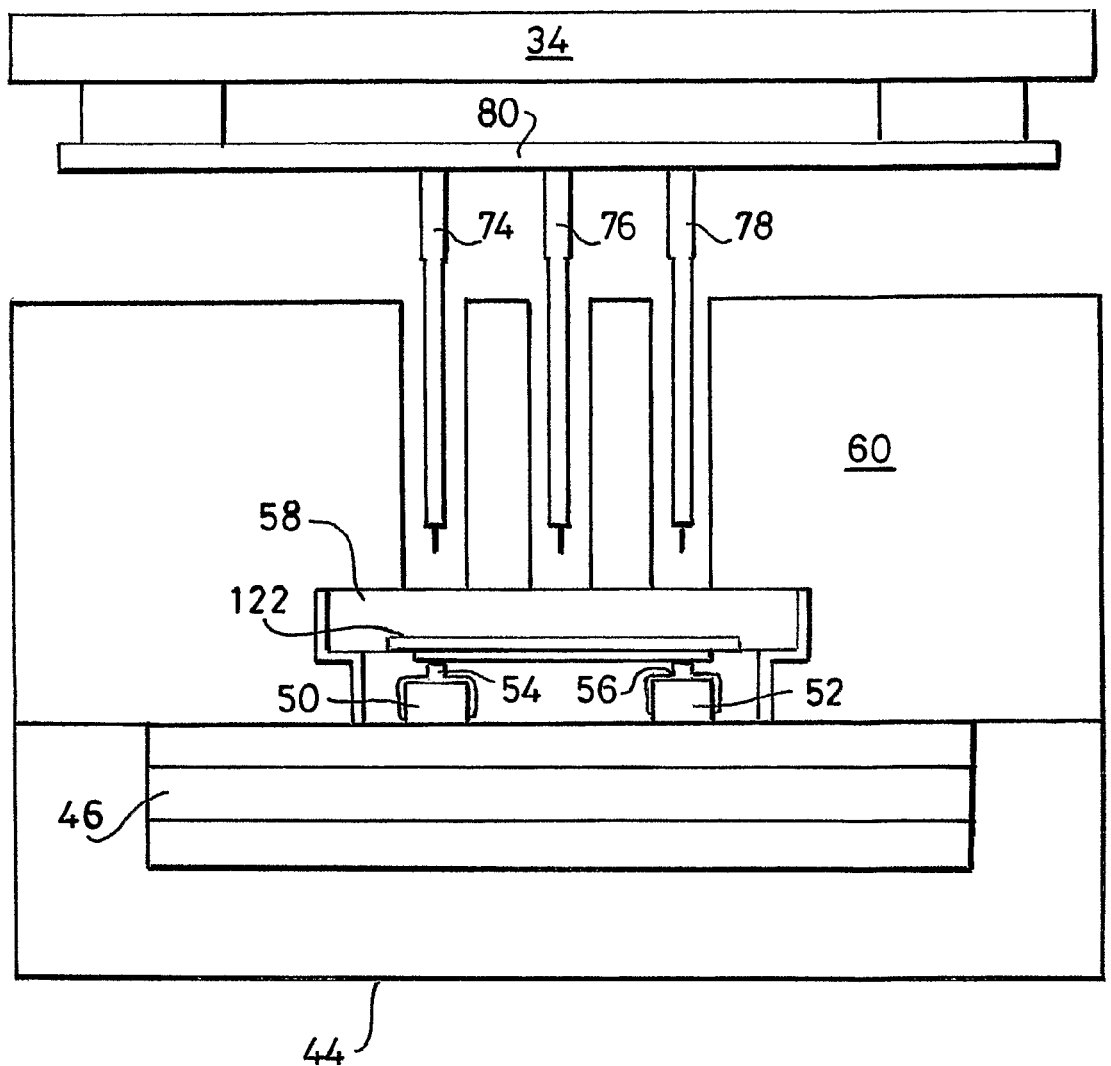
FIGS. 7 and 8 are front sectional views of certain parts of the apparatus of FIG. 3 at the stages of operation shown in FIGS. 5 and 6 respectively.
Figure 8:
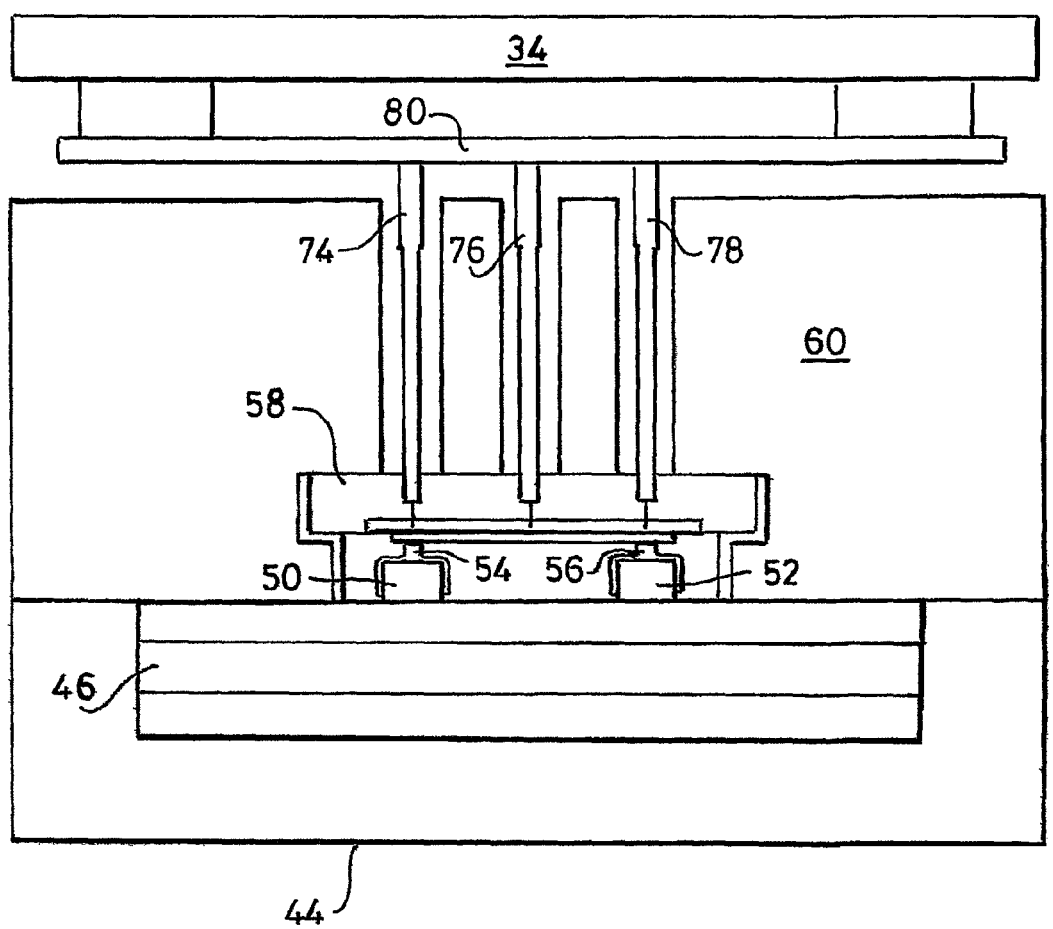

The docking mechanism can accept two cartridges side by side. The apparatus thus has two recesses in the cassette mounting block, each for a respective cartridge, two pairs of ferrules on the microfluidic manifold and two sets of three electrical connectors extending from the overhead PCB. These elements are identical to each other, and only one set of the elements has therefore been described. The corresponding reference numerals followed by an apostrophe are used to denote the elements in the other set. For the sake of simplicity only one set of the elements is shown in FIGS. 7 and 8.

Figure 9:
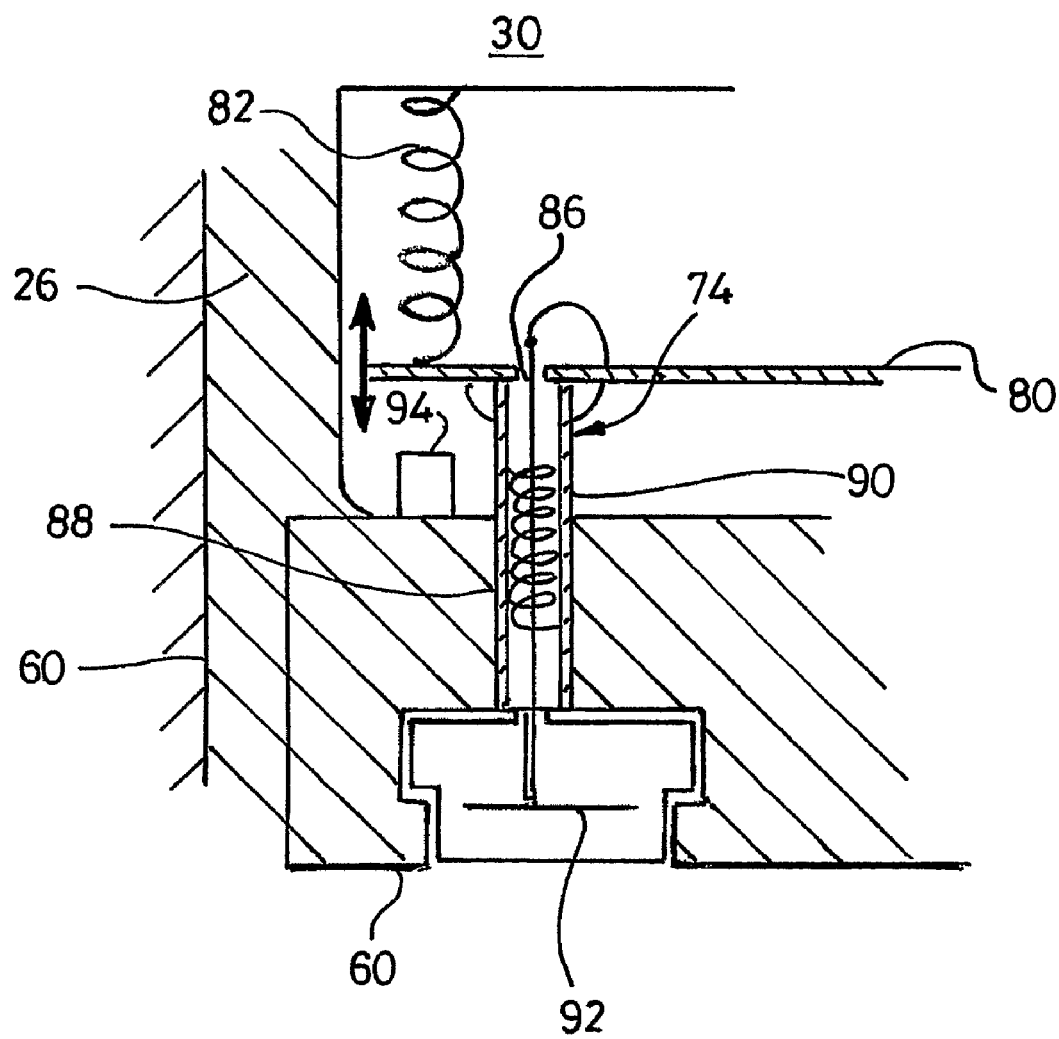
FIG. 9 is a detailed front sectional view of part of the docking mechanism, showing in particular an electrical connector.

Referring back to FIG. 3 the three electrical connectors 74, 76 and 78 (of said one set of elements) take the form of coda pins, one of which, the pin 74, is shown in more detail in FIG. 9. The coda pin is in the form of an assembly in which a central elongate connecting pin 86 is slideably mounted in a plastics sleeve 88 of, for example, PTFE, PolyAcetal, or Nylon. A downward biasing force is exerted on the pin 86 by a compression spring 90 secured at one end of the inner periphery of the sleeve 88 and at the other to the pin 86. Sleeve 88 helps to locate the pin 86 prior to the latter making connection with a transducer 92 forming part of a cartridge in the docking mechanism. As can also be seen from FIG. 9, the cartridge mounting block 60 carries a dead stop 94 (another similar stop being provided on the other side of the block 60) for limiting the extent of allowable downward movement of the board 80.

Figure 10:
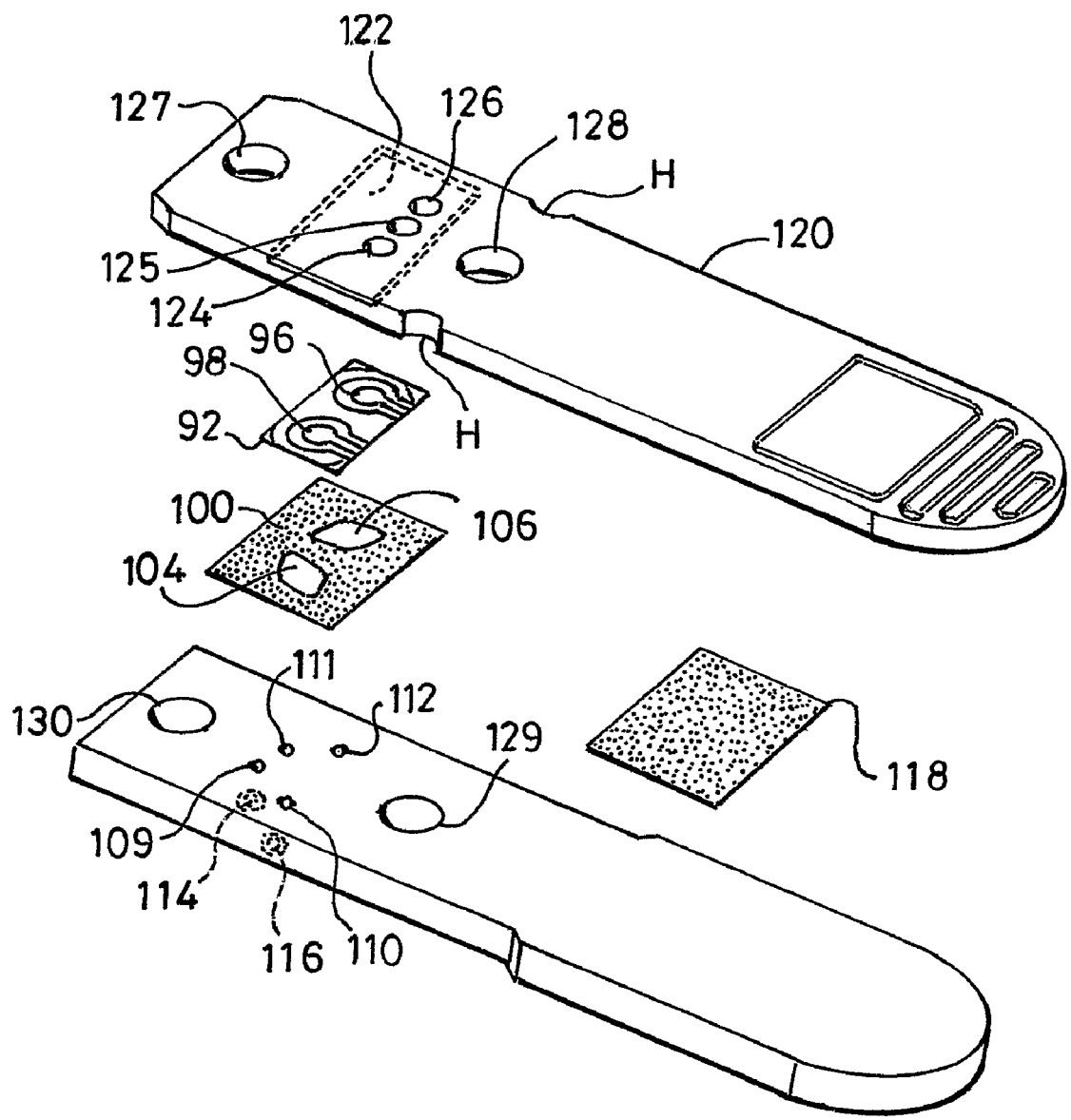
FIG. 10 is an exploded perspective view of a cartridge of the apparatus.
Figure 11:
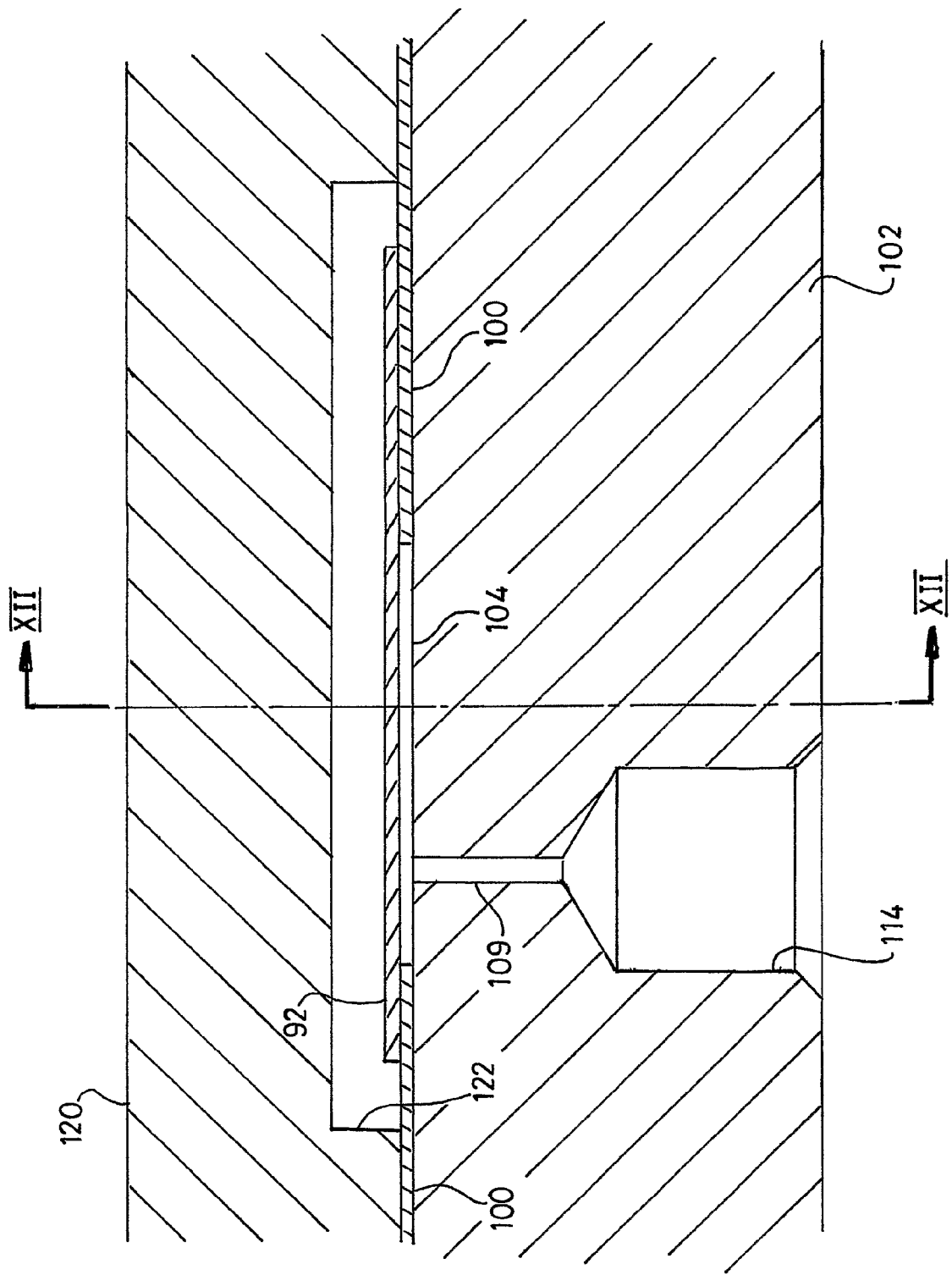
FIG. 11 is a sectional side view of the cartridge shown in FIG. 10.
Figure 12:
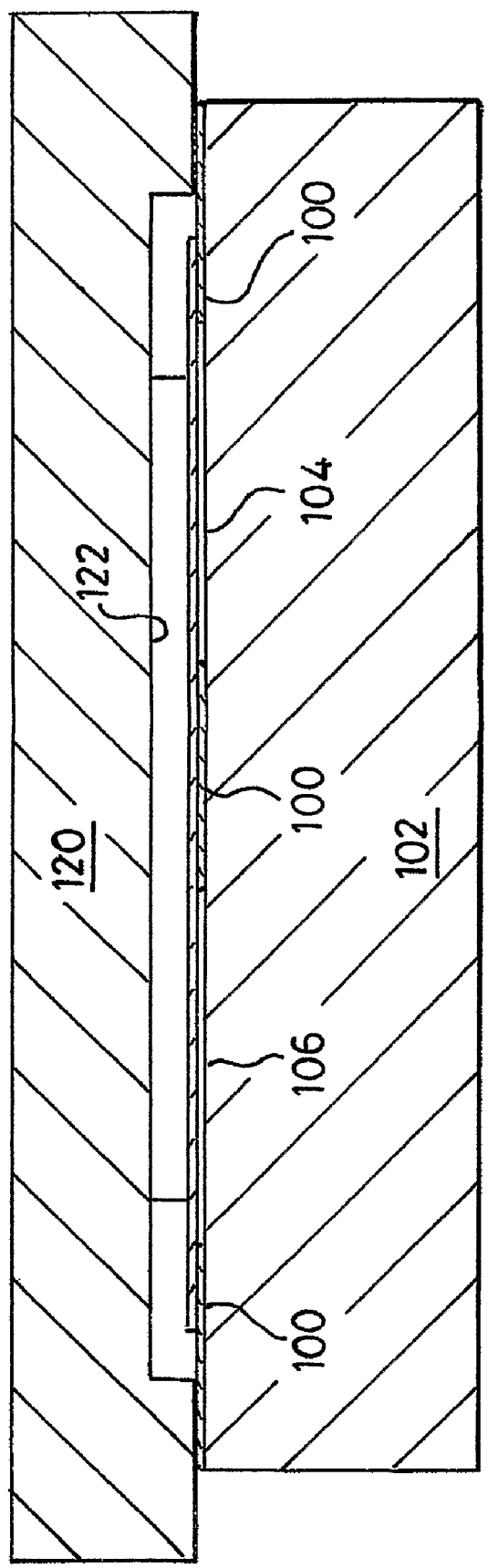
FIG. 12 is a sectional end view of the cartridge, taken along the line XII-XII of FIG. 11.
Figure 17:
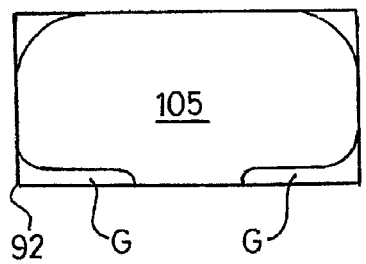
FIG. 17 is a view of the underside of the quartz crystal wafer (and the electrode thereon) used in the cartridge of FIGS. 10 and 11.

As is indicated above, the transducer 92 forms part of a cartridge, which is shown in more detail in FIG. 10. The transducer comprises a quartz crystal plate. The plate is coated on one surface with gold in a pattern that defines a pair of drive electrodes 96 and 98, each of which is in registry with a respective one of two separate flow cells. The underside of the plate is also coated with gold to form a common earth electrode (105 in FIG. 17) on the ceiling of the flow cell. The top surface of the plate carries a further gold coating which has two keyhole shapes openings in which the drive electrodes (and their connection strips 99 and 101) are situated, and are spaced from coating 97. The coating 97 extends around the edge 103 of the crystal to provide a contact for enabling a coda pin engaging the top surface of the plate to connect to the earth electrode underneath. The common earth electrode on the underside of the crystal carries a binding layer (not shown) for binding with a target substance.

The underside of the transducer 92 is adhered to the top surface of an adhesive membrane 100 the underside of which is adhered to a plastics plate 102 the upper surface of which constitutes a support surface for the transducer 92.

The membrane 100 is a three layered structure comprising a carrier layer of 12 microns thickness sandwiched between upper and lower adhesive layers, each of approximately 36.5 microns thickness. An example of suitable material for the membrane is the double sided adhesive tape sold under the trademark FASTOUCH. Adhesive membranes of various thicknesses, greater or less than 85 microns are available, which can be used to control the height of the flow cell. The membrane 100 has two apertures 104 and 106.

The shape of the apertures, and hence each flow cell is arranged to provide a suitable profile to ensure laminar flow conditions over the surface, for example the diamond shape illustrated, but other shapes may be designed by those skilled in the art of fluidic design. Each of the apertures 104 and 106 is in registry with a respective electrode 96 and 98, and thus with an active area of the quartz crystal, i.e. an area of the common earth electrode in registry with one of the electrodes 96 and 98. The membrane 100 spaces the transducer 92 from the upper surface of the plate 102 so that there is a small gap between each of two said active areas of the quartz crystal and the upper surface of the plate 102, each gap being bounded by the edge of a respective one of the two apertures 104 and 106. Each gap constitutes a respective flow cell which communicates with a respective pair of inlet/outlet passages 109-112 in the plate 102. Passages 109 and 111 are inlet passages, whilst passages 110 and 112 are outlet passages. Each passage leads onto a female connector, such as the connectors 114 and 116 which is generally cylindrical and has a tapered end portion, each of the connectors being arranged to receive a respective ferrule of the fluid delivery/removal system. Either or both of the flow cells may be used for the sample to be analysed. Alternatively one may receive the sample, the other a reference solution.

As can be seen from FIG. 10, the inlet and outlet for each flow cell are located at opposite end regions of the latter. Consequently, a sample introduced into the inlet of the flow cell will flow along the length of the flow cell to the outlet, during which period the sample will interact with the active surface of the crystal and the effect of that interaction will be measured.

As can be seen from FIG. 10, the flow cells are situated towards one end of plate 102, towards the other end of which there is provided a patch 118 of the same material as the membrane 100. The purpose of this patch is to help to adhere a top plate 120 (of a plastics material) to the bottom plate 102. The top plate 120 includes a recess 122 which, in the assembled cartridge, accommodates the sensor 92 so that the latter makes no contact with the plate 120. The membrane 100, however, does extend beyond the boundaries of the recess 122 so as to adhere the two plates 102 and 120 together at their forward ends.

As well as securing the transducer 92 in position and defining each flow cell, the membrane 100 provides a suitable seal, by virtue of the adhesive layers, for preventing fluid escaping from the flow cells.

The upper plate 120 includes through bores 124, 125 and 126 through which, in use, the coda pins extend to make contact with the electrodes 96 and 98 and the common earth contact of the transducer 92. Notches H in the upper plate serve to provide an initial location of the cartridge in the docking station as will be described below.

The two plates 102 and 120 also include large diameter through bores 127-130, the bore 127 in the plate 120 being in line with the bore 130 in plate 102, the bore 128 with the bore 129 so that there are two large bore through passages in the cartridge housing (defined by the plates 102 and 120). These passages, in use, accept electrically conductive lateral location pins (e.g 47, 49) of the docking mechanism for assisting in the correct location of the cartridge. The lateral location pins when extended into and past the cartridge engage opposed earth pins on the circuit board 80, and thus also to act as a Farraday cage around the drive Coda pins and electrodes of the sensor. The spacing between the pins is chosen, based on the frequency of the drive signal to the sensor, to achieve that end.

Figure 3:
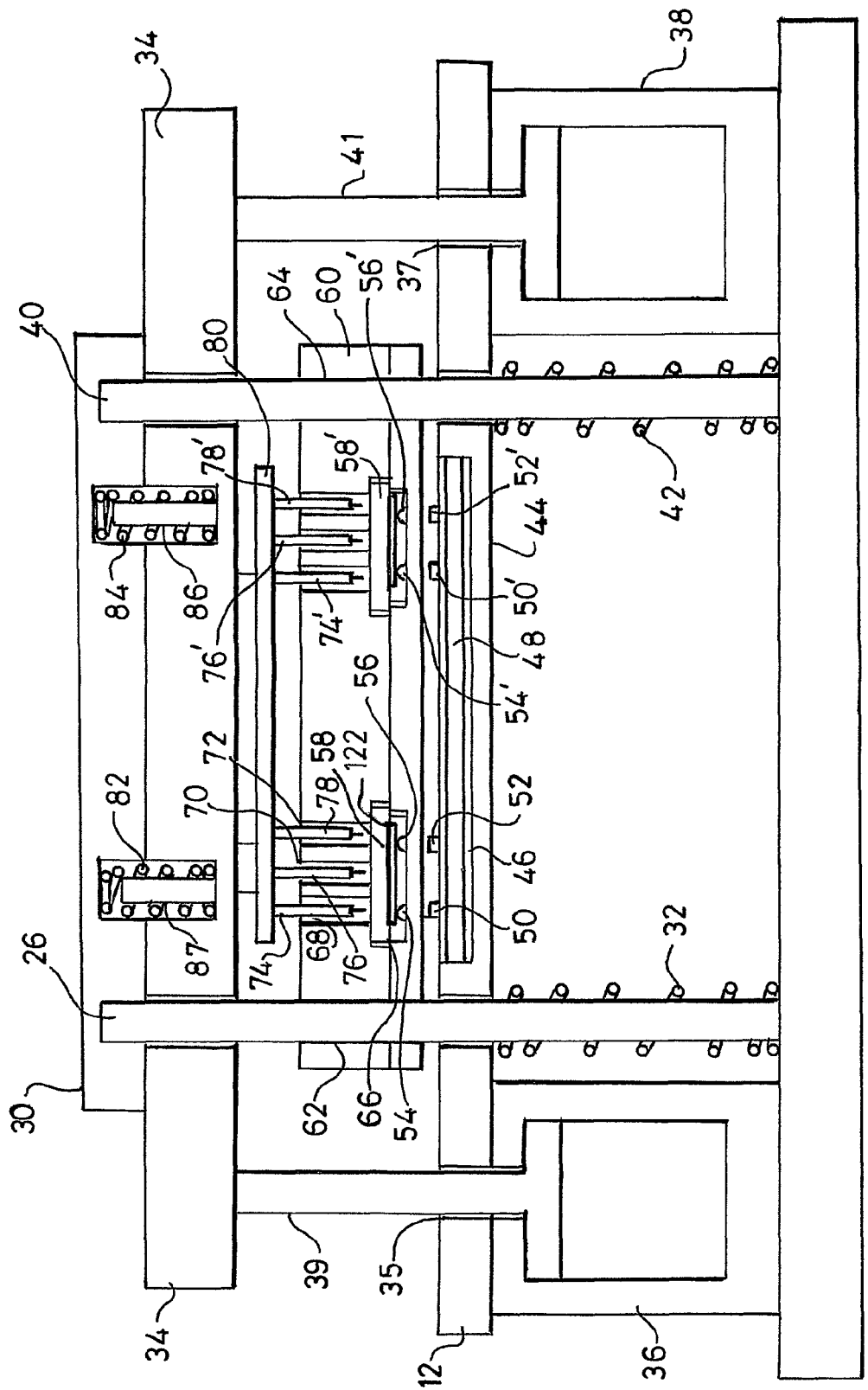
FIG. 3 is simplified sectional front view of the docking station at the stage of operation shown in FIG. 4.

Before a cartridge is inserted into the docking mechanism, the hydraulic/pneumatic cylinders 36 and 38 are extended to urge the upper carrier plate 34 and lower carrier member 12 away from each other against action of the springs 32, 42, 82 and 84. This moves ferrules 50 and 52 and the coda pins 74, 76 and 78 clear of the slot 66 in the cartridge mounting block 60 so that a cartridge can be inserted into the latter. This thus puts the docking mechanism into a condition into which a cartridge can be received or removed. FIGS. 1, 3 and 4 illustrate the docking mechanism when in that condition.

The cartridge 58 is then slid into one of the channels 8, 10 of the cassette location bar 6, and is moved into the slot 66 until the inboard end of the cartridge 58 abuts the end of the slot. It will be appreciated that the docking mechanism for the cartridge shown in FIG. 10 will have a sufficient number of electrical and fluidic connectors to provide electrical/fluid connection to both flow cells in the cartridge.

After a cartridge has been inserted into the docking mechanism, the pressure in the fluid (hydraulic or pneumatic) being used to extend the cylinder 36 and 38 is released so that both cylinders no longer exert any substantial separating force between the carrier member 12 and plate 34. As a result, the movement of the plate 34 and member 12 is determined by the action of the springs 32, 42, 82 and 84. Since the springs 82 and 82 are considerably weaker than springs 32 and 42, the springs 32 and 42 act on the plate 34 (through the plate 44, and the shafts 39 and 41 of cylinders 36 and 38) to retain the plate 34 in its retracted position. However, at the same time as the cylinders 36 and 38 retract, the springs 32 and 42 also move the carrier member 12 upwards towards the cartridge mounting block 60. This movement continues (whilst the plate 34 remains stationary) until the ferrules on the fluidic manifold 48 engage the female fluid connectors in the bottom plate of the cartridge. The springs 32 and 42 urge the ferrules into the female connectors with sufficient force to cause the ferrules to form liquid tight seal.

Figure 2:
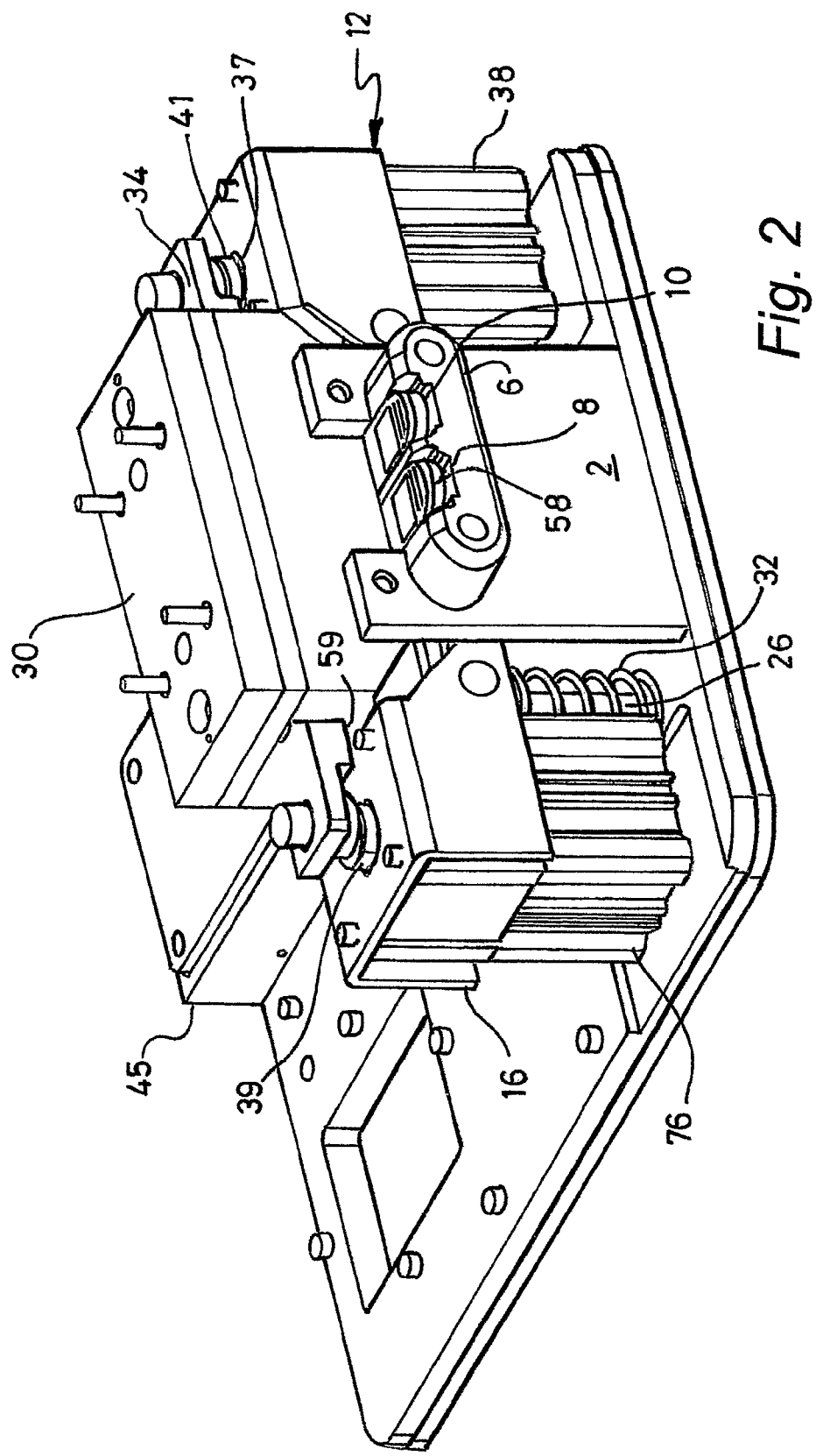
FIG. 2 is a similar view of the docking station, but showing two cartridges inserted therein and with the clamping mechanism in its closed condition.
Figure 6:
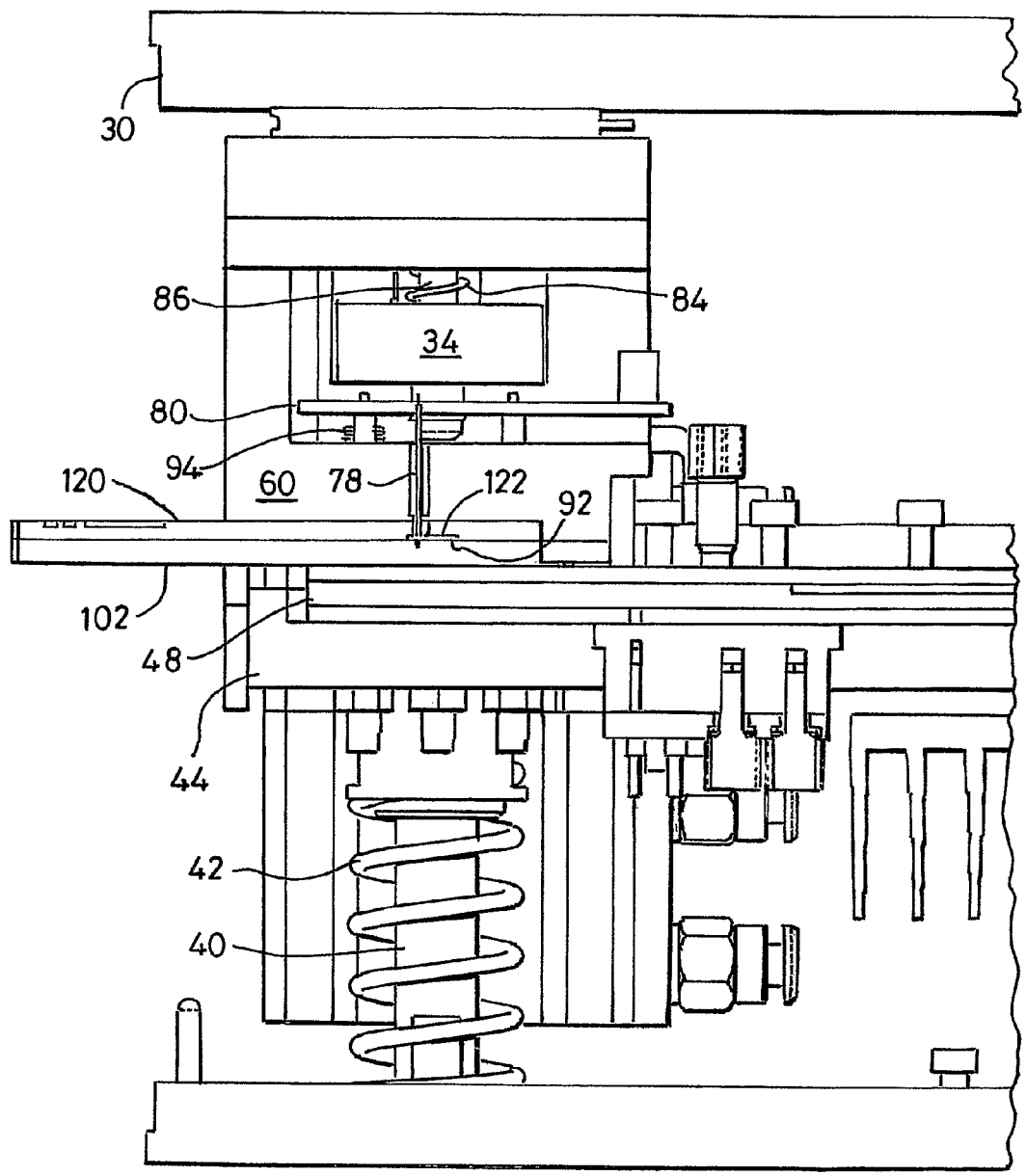

This condition is illustrated in the docking mechanism shown in FIG. 4 and in the simplified schematic arrangement of FIG. 7. The plate 44 engages the block 60 so that further upward movement of the plate 44 is prevented. At this stage, the springs 32 and 42 can no longer act on the plate 32 through the cylinders 36 and 38 so that the plate 34, and hence the PCB 80 and the coda pins 74, 76 and 78, moves down towards the cartridge under the action of springs 86, 87. As a result, each coda pin extends into a respective aperture of the cartridge upper plate to engage a drive electrode or, as the case may be, the earth contact on the transducer. The plate 34 continues to move down until the downward movement of the corner plate 34 is prevented by contact with the base of a transverse slot 59 in the mounting block 60. The height of this slot is selected to ensure that the good contact is made by the spring loaded coda pins on the sensor, and acts as the dead stop 94 shown in FIG. 9. This condition of the mechanism is shown in FIGS. 2, 6 and 8.

Since the cartridge is located separately from the plate 44 and 34, the relatively large force exerted by the plate 44 on the cartridge (to obtain a fluid seal), does not result in any large reaction force between the coda pins and the transducer. Thus the invention enables an effective and reliable fluid seal to be provided without exerting large forces on the transducer.

Figure 13:
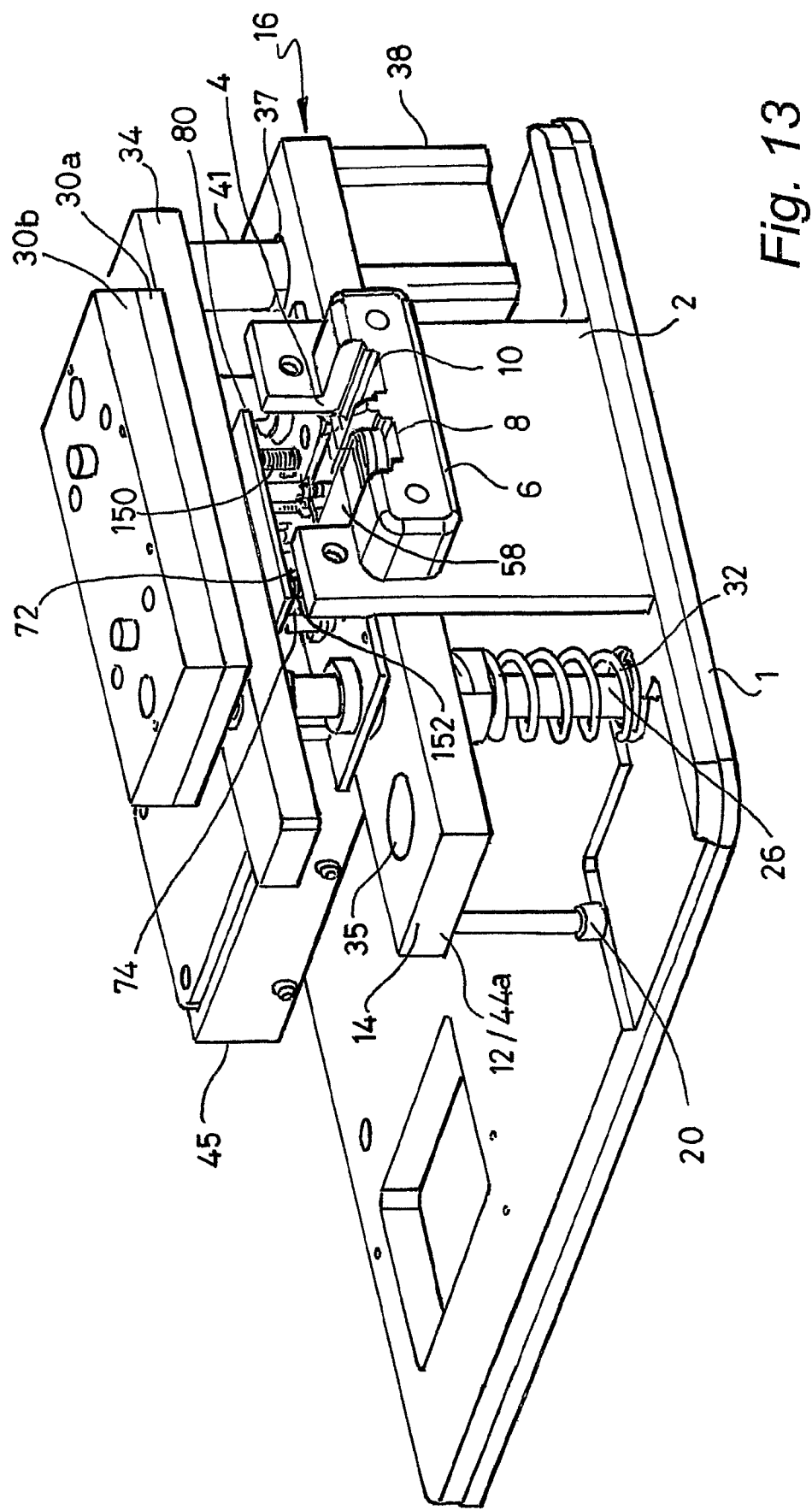
FIG. 13 is an isometric view, corresponding to FIG. 1, of a second embodiment of docking mechanism in accordance with the invention.

The embodiment of docking mechanism shown in FIG. 13 is similar in many respects to the embodiment shown in FIGS. 1-9. Therefore, in FIG. 13, components corresponding to those shown in FIG. 1-9 are denoted by the same reference numerals as are used in those figures. In FIGS. 13 and 14 the block 60 has been omitted to enable the electronic contacts to be shown. The mechanism has two pneumatic/hydraulic actuator cylinders corresponding to cylinders 36 and 38, but the cylinder 36 has been omitted from FIG. 13 to enable the post 26 and spring 32 to be seen. In addition the mounting plate 34 whilst present in this embodiment, has been omitted from FIG. 14 for the sake of clarity.

In the first embodiment, the carrier member 12 comprises a sub-assembly of two U-shaped end portions 14 and 16 to which a central plate portion 44 is bolted. In the FIG. 13 embodiment, however, the sub-assembly has been replaced by a single flat plate referenced 12/44a, the end regions of which are denoted by reference numerals 14 and 16 (but are not U-shaped). Each actuator cylinder has a body which is attached to the underside of the plate 12/44a by means of four vertical bolts, one of which is shown at 20 in FIG. 13.

In the embodiment shown in FIGS. 13 and 14 the carrier member (i.e. the mounting plate 34) is mounted on slidable bushes B1 and B2 which run on rods 26 and 40. Screw heads S1 and S2 are recessed into apertures in plate 34 and hold the spring in its compressed state, against plate 30. Various rods R1-5 are used to precision align the carrier plate 34 with respect to block 60 Stub pin P is one of several similar (others not shown) to precision attach the PCB 80 to plate 34, i.e. to define a fixed vertical distance between plate 34 and the PCB 80.

To assist location of the cartridge a screw 150 comprising an internally spring loaded ball bearing 150a is aligned to locate with notches H in the side of the cartridge and provide positive feedback to the user that the cartridge is properly located.

Screw connectors N1 and N2 attach plate L to the block 60. Plate L is fixed with respect to the frame. This plate provides a continuation of the T shaped channels 8 and 10 from bar 6 into the docking station (i.e. mechanism). Upper plate 30 comprises two parts, a lower part 30a and an upper part 30b, which face each other along a longitudinal phase. In FIG. 14 the part 30a has been removed. In this embodiment a peltier cooling device E is located on top of 30b and in good thermal contact with it. This assist in dissipating heat generated on the PCB 80. Screw connections M1 and M2 connect 30a and 30b and allow the plate 30b in turn to be attached to an exterior frame plate. Stub pin T and a corresponding one on the other side of the 30b precision space the plate 30b from an external cover to allow for the thickness of the cooling device E.

Other parts visible in FIGS. 13 and 14 include electrical connectors C to the PCB 80.

Figure 15:
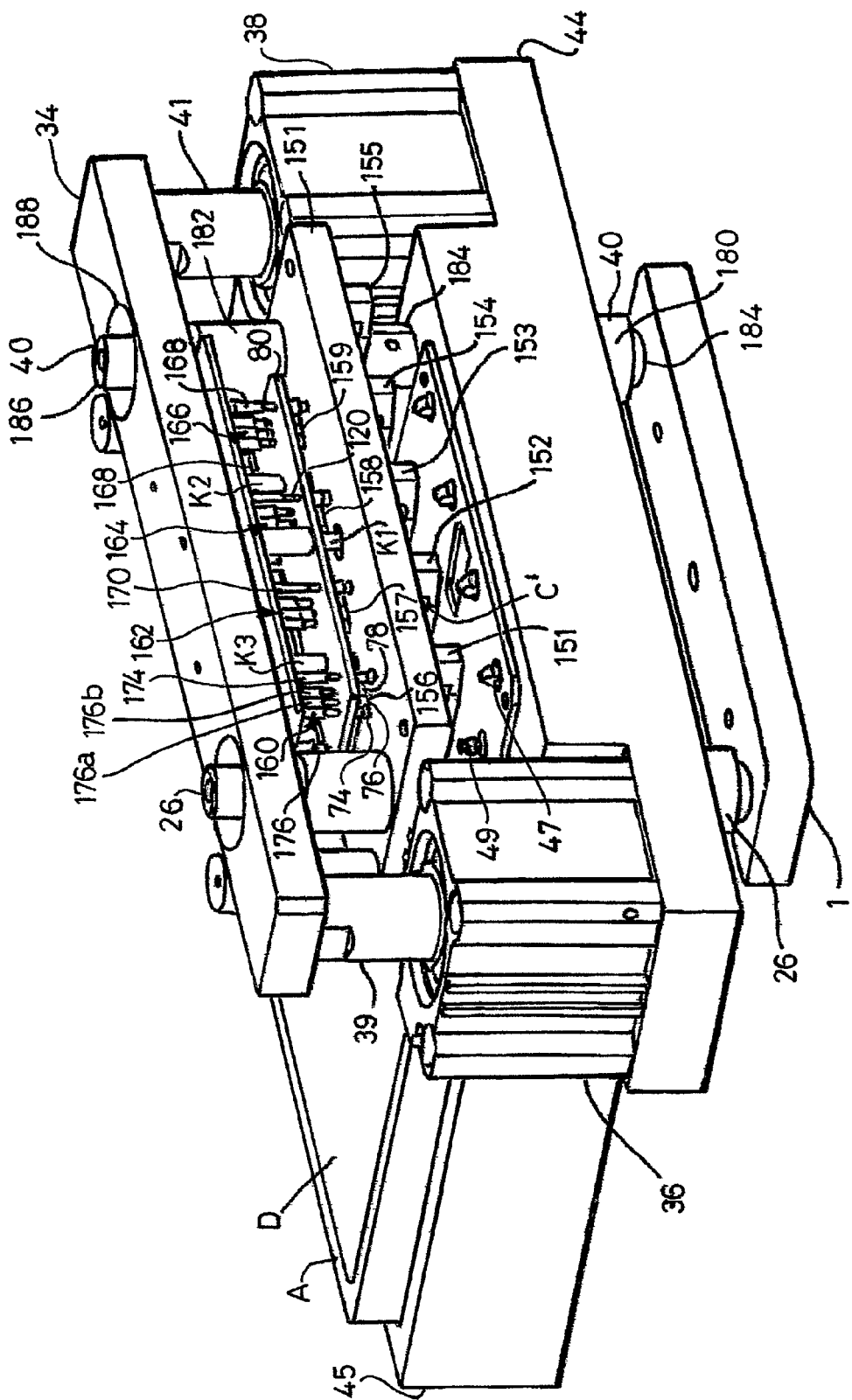
FIG. 15 is an isometric view of a third embodiment of docking mechanism in accordance with the invention.
Figure 16:
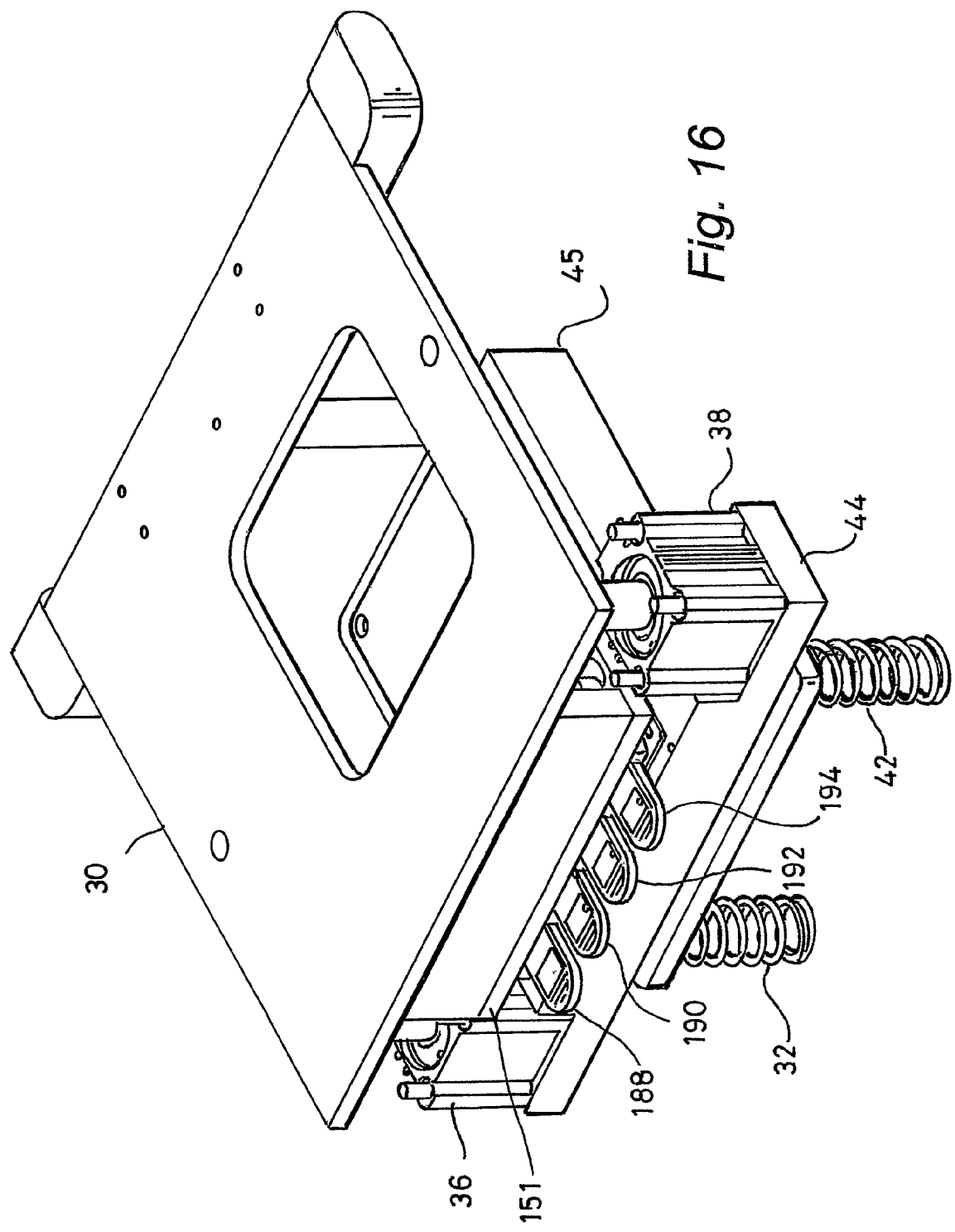
FIG. 16 is an isometric view, from a higher angle, of the third embodiment with four cartridges inserted therein.

The embodiment of docking mechanism shown in FIGS. 15 and 16 is operable to receive four cartridges of the type described above, and is thus for use with an eight channel analyser (two channels per cartridge).

This embodiment of docking mechanism has numerous features which correspond to features of the other two embodiments of docking mechanism, and are therefore denoted by the same reference numerals as have been used in relation to the other embodiments. Thus, for example, the third embodiment has two hydraulic or pneumatic actuating cylinders 36 and 38 which act between a lower plate 44 carrying ferrules and fluid supply manifold and a upper plate 34 which carries the PCB 80. In this case, however, the bases of the actuating cylinders 36 and 38 are attached to the plate 44.

The cylinders 36 and 38 flank a reference plate 151 attached to a frame of the machine that includes the base plate 1 and the upper plate 30 (FIG. 16). The underside of the reference plate 150 carries five vertical, parallel plastics strips 151-155. The opposing sides of adjacent strips carry grooves for accepting cartridges so that the apparatus accept four cartridges, each retained in the grooves between a respective neighbouring pair of the strips. The plate 151 also includes four slots 156-159 through which a respective group of three electrodes extend so as to be able to contact the terminals on a crystal in a cartridge under the plate 151. One group of the electrodes is denoted by the reference numerals 74, 76 and 78, the other electrodes are identical, and all of the electrodes are identical to those used in the other embodiment described above. In the embodiment shown in FIGS. 15 and 16, the circuit board 80 by which the immediate connection to the crystal is made is entirely passive. The active components for driving and sensing the crystals have been removed to the second upper circuit board 161 positioned above the board 80. The upper board carries four sets of three electrical connectors, generally referenced 160, 162, 164 and 166 which provide connections between the electrical connectors on the lower board 80 and a separate analyser (not shown) for providing the power to drive the crystals in the cartridges and analysing the resultant signals. Thus 176 and 176b are the active drive connections to the board 80 and 176a is the earth connection to the board.

The upper board also carries earth connectors 168, 170, 172 and 174 for providing earth connections for the earth pins, e.g. 47. The lower passive board 80 is mounted to the upper active board by metal connecting pins, K1-3. These are also earthed on both the upper and lower boards, and together with the earth connectors 168, etc form a Faraday cage around the driving connectors between the two boards. The Faraday cage around the cartridges is formed by the earth pins and cartridge locating pins, as with the other embodiments.

The assembly 44 comprises a mounting section 45 for housing the microfluidic manifold, made of Acetal plastic. The manifold is located in an aluminium insert A to provide rigidity and thermal control under the cover plate D. The manifold connects the macro fluid delivery system to the eight pairs of ferrule connectors (not shown). and hence to the four flow cells of the cartridges in the docking mechanism.

Each of the support posts 26 and 40 is of a stepped construction, and only this aspect of the support post 40 will be described. That post has an enlarged diameter lower portion 180 separated from a further, upper enlarged diameter portion 182 by a reduced diameter portion 184. The compression spring 42 acts between the base plate 1 and the underside of the plate 44, which is slideably mounted on the reduced diameter portion 184, so that the spring exerts an upward biasing force on the plate 44. The upper surface of the reference plate 151 is attached to the enlarged diameter portion 182 and thus to the frame of the machine.

The top of the post 40 has a further reduced diameter portion 186 which extends through an aperture 188 in the plate 34. That aperture contains a radially inwardly directed flange (not visible) which is of an inner diameter slightly larger than that of the portion 186 and which provides a shoulder for a spring (corresponding to spring 84) which acts between the shoulder and the underside of the top plate 30 to exert a downward biasing force on the plate 34. For the sake of clarity all of the springs have been omitted from FIG. 15, although the springs 32 and 42 are shown in FIG. 16 (from which the base plate 1 and columns 26 and 40 have been omitted).

The operation of the docking mechanism is similar to that of the other embodiments described above. More specifically, the cartridges are inserted into the spaces between the strips 151-155, while the actuators 36 and 38 are in an extended condition, as shown in FIG. 15. The four cartridges are shown at 188, 190, 192 and 194 in FIG. 16, and are orientated with the openings for the electrical contact pins uppermost and the female fluidic connectors on their underside. The cartridges are located by sliding into opposed recesses (one of which is denoted C' in FIG. 15) located on the sides of strips 151-155. Part way down these recesses are located spring loaded ball bearings which locate in the notches H in the side of the cartridge as it is pushed into the recess, and so positively locates the cartridge. The actuators are then retracted, causing the springs 32 and 42 (which are stronger than the springs acting on the plate 34) to move the plate 44 up against the underside of the cartridges so that, initially, the fluidic connections are established. As the actuators 36 and 38 continue to retract, the springs acting between the plates 34 and 30 urge the plate 34 downwards so that the Coda pins engage the electrical contacts on the quartz crystals in the cartridges and so that the earthed upper pins engage the corresponding, aligned earthed lower pins (e.g. 49 and 47) to create a respective Faraday cage around each cartridge.

Figure 18:
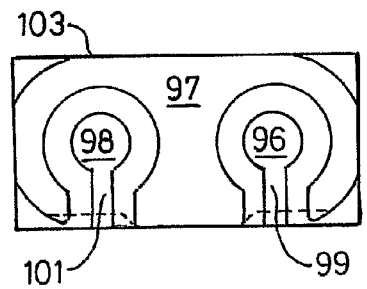
FIG. 18 is a plan view of the crystal (showing the other electrodes)
Figure 19:
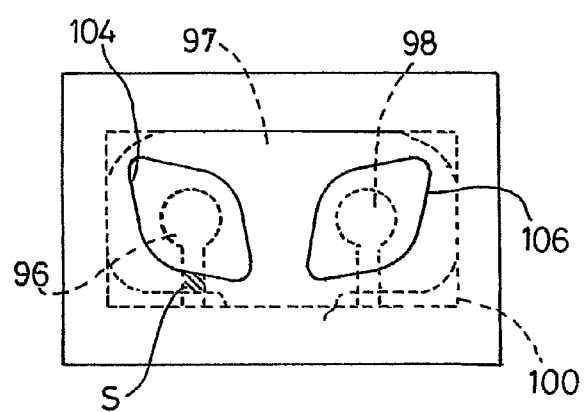
FIG. 19 is a view of the underside of the crystal with an adhesive membrane thereon.

The embodiment of sensor (shown in FIGS. 17-19) has a dual channel sensing plate 92 of quartz which carries an active gold layer on either side. The biochemically active side of the sensor coated with a continuous coating of gold and is connected to earth. the electrically driven side has a pattern in which the active areas (96 and 98) are circular, with contiguous rectangular areas 99 and 101 extending to the edge of the quartz plate. These rectangular areas provide four electrical contacts between the active electrodes and the Coda pins in the docking mechanism. The electrically active side (i.e. the side carrying the circular electrodes) is also provided with a "guard" earth electrode 97 which forms a respective ring around each driven circular area and serves to dampen any electrical cross-talk between the two or more resonators.

In use, the electrical drive applied to the circular electrodes (through the rectangular areas) causes the quartz plate to resonate. This resonance occurs where the electrically driven electrode opposes the ground plate electrode. Conventionally, this causes a transfer shear mechanical mode to be set up under the circular areas of the driven electrodes.

Applicants have discovered, however, that the presence of the drive signal in the rectangular areas can cause the plate under these areas also to oscillate where the ground plain also opposes the rectangular areas. More particularly, with reference to FIG. 19 (which shows the overlay between the adhesive membrane and the electrodes), the region of each rectangular electrode between the edge of the earth electrode 105 and the edge of the flow cell (e.g. the shaded area S in FIG. 19) can give rise to oscillations which can either be reflected off the edge of the crystal 92 or place stresses on the crystal (by virtue of the restraining effect of the adhesive membrane). These effects can vary over time, be hard to predict and therefore are detrimental to the accuracy of the instrument.

The effects are at least mitigated by the spacing of the bottom portion of the electrode 105 (as viewed in FIG. 17-19) from the bottom of the crystal 92 so that there is at least an area G at the edge of the crystal where the rectangular portions do not overlap the earth electrode and therefore do not cause the unwanted vibrations.

An improved version of the sensor (forming part of the cartridge) shown in FIGS. 20-22 will now be described.

Figure 20:
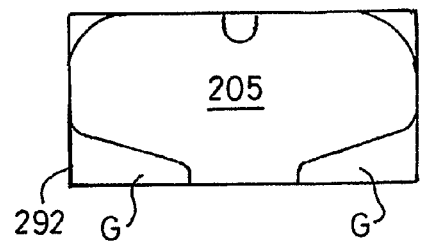
FIGS. 20-22 are views corresponding to FIGS. 17 to 19 respectively, of a modified version of crystal, membrane and electrodes.
Figure 21:
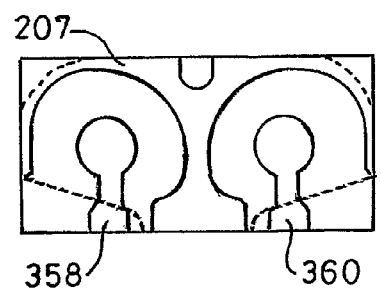
Figure 22:
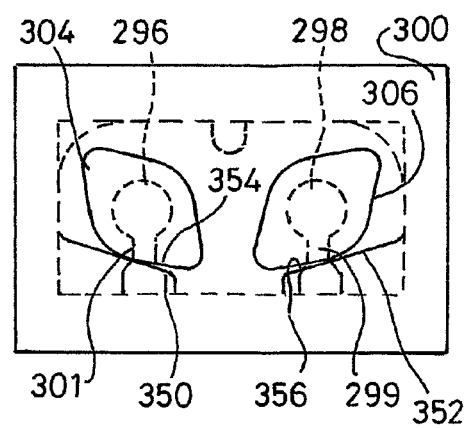

The improved resonator design shown in FIGS. 20-22 has many features in common with or corresponding to those of the design shown in FIG. 7-19, and these are denoted by the reference numerals used in FIG. 7-19 raised by 200.

In this case, further portions of the earth electrode 205 have been removed where these overlap with the rectangular areas 299 and 301 of the driven electrodes. This change means that there are little or no areas of opposing driven and earth electrodes where the membrane 300 touches the crystal plate 292. Thus the area of crystal under the rectangular portions and in contact with the adhesive membrane does not significantly oscillate when the sensor is driven. As a result, the resistance of the quartz plate at resonance is not affected by damping caused by the presence of the membrane contacting this area, and a lower resistance and higher Q factor are achieved.

These improvements illustrated in the graph of FIG. 23, in which the left-hand column of each graph shows the resistance or, as the case may be, Q factor of the first embodiment sensor, whilst the right hand column of each graph shows a corresponding measurement for the improved version.

As can be seen from FIG. 22, the lower edges 350 and 352 of the electrode 205, i.e. the edges which extend across the rectangular portions 301 and 299, are inclined in the same sense as the corresponding adjacent edge 354 and 356 of the aperture in the membrane, and hence the flow cell. Thus, the edges of the electrode substantially conform to the adjacent edge of the flow cell, thereby further reducing the overlap mentioned above.

The result of the improvements discussed above is that the sensor, when used in contact with a liquid, has reduced noise and improved unit to unit variance. Additionally, it has been found that the elastic properties of some adhesives may change with time, and that this can give rise to slow changes in the damping of the resonator if substantial portions of the crystal under the membrane are vibrated. This is also undesirable as it leads to baseline drift. With the improved design, the changes in the elastic or mechanical properties of the adhesive or the membrane have a much reduced effect. This can contribute to improved baseline stability and drift which is important in certain types of biochemical assay.

The improvements are optimised when the edge of the membrane does not overlap the edge of the modified electrode boundary at all. However, improvements over the earlier design are also achieved where there is a significant reduction of overlap. It is desirable not to extend a flow cell boundary too far outside the electrode boundary because this exposes uncoated quartz to the analyte fluid. This may result in non-specific absorption of coatings and the like to the quartz which is undesirable.

It can also be seen from FIGS. 21 and 22 that the outboard ends 358 and 360 of the rectangular portions are of an enlarged width. This improves the tolerance of the analytical apparatus to changes in alignment between the Coda pins and the electrodes.

Figure 24:
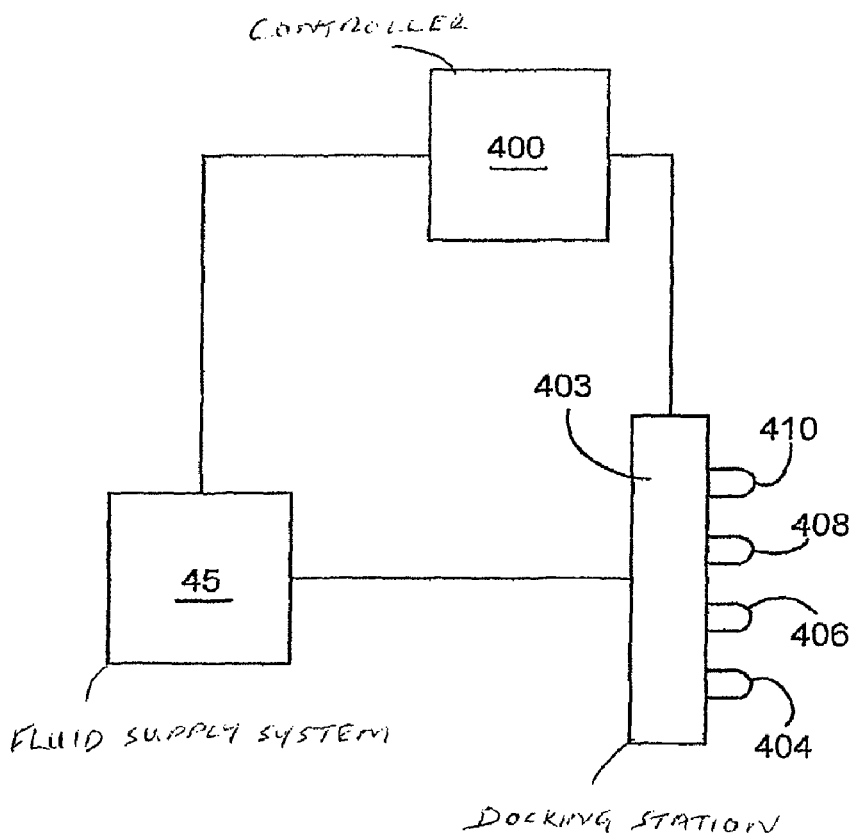
FIG. 24 is a block diagram of analysing apparatus also in accordance with the invention.

The analytical apparatus shown in block diagram form in FIG. 24 comprises a docking station, referenced 403, of the type shown in FIGS. 14 and 15 connected to a fluid supply system 45 (also shown in those figures). The operation of the fluid supply system 45 is controlled by a controller 400 which is also connected to the docking mechanism 403, and controls the operation of the actuating cylinders 36 and 38, selectively to open and close the mechanism. In FIG. 24, the mechanism has received four cartridges, 404, 406 and 408 and 410, which are clamped in position in the docking mechanism. The controller 400 also controls the circuitry on the board 80, so as to drive the sensors in the cartridges, and receives the signals resulting from the oscillation of the sensors, which are then analysed in the controller 400.

The invention claimed is:

1. A docking mechanism for releasably receiving a cartridge for use in analysing a sample comprising a fluid, the cartridge having a flow cell for the sample and an electrically operated sensor for performing said analysis, the docking mechanism comprising a clamping mechanism for urging fluid connector means against the cartridge to provide a fluid connection between the flow cell inlet and sample delivery means; the docking mechanism also comprising an electrical connector for engaging the sensor to connect the latter to electrical circuitry for operating the sensor, the electrical connector being movable, towards and away from the sensor, relative to the clamping mechanism, so that, in use, the electrical connector exerts on the sensor a force which is sufficient to maintain the necessary electrical connection, whilst not being so great as to have a substantial detrimental effect on the accuracy of the sensor, wherein the mechanism includes earthed pins for forming a Faraday cage around the electrical connector and the sensor, and wherein the earthed pins are also operable to locate the cartridge in an operable position in the mechanism.

2. A docking mechanism according to claim 1, in which the clamping mechanism comprises a carrier member and a co-operating surface, at least one of which is movable towards and away from the other, releasably to compress a cartridge therebetween.

3. A docking mechanism according to claim 2, in which the carrier member carries the fluid connector means.

4. A docking mechanism according to claim 3, in which the fluid connector means comprises a connector so sized and shaped as to make mating engagement with a complementary connector on a cartridge.

5. A docking mechanism according to claim 4, in which the fluid connector means of the docking mechanism is a male connector.

6. A docking mechanism according to claim 5, in which the male fluid connector comprises a tube which is, in use, inserted into a bore in a cartridge received in the docking mechanism.

7. A docking mechanism according to claim 6, in the tube is a ferrule.

8. A docking mechanism according to claim 3, in which the fluid connector on the carrier member is one of two such connectors for respective connection to an inlet and an outlet of a flow cell of the cartridge.

9. A docking mechanism according to claim 2, in which the docking mechanism includes actuation means for automatically closing and opening the clamping mechanism, respectively to clamp and release the cartridge.

10. A docking mechanism according to claim 9, in which the actuation means also acts on the electrical connector automatically to move the connector into and out of engagement with the sensor.

11. A docking mechanism according to claim 10, in which the actuation means comprises a drive assembly which acts between the electrical connector and the carrier member to alter the separation therebetween.

12. A docking mechanism according to claim 11, in which the co-operating surface is interposed between the carrier member and electrical connector, and in which the drive assembly is fixed in position relative to the co-operating surface.

13. A docking mechanism according to claim 11, in which the drive assembly comprises a hydraulic or pneumatic gas cylinder.

14. A docking mechanism according to claim 11, in which the clamping mechanism includes a clamping mechanism biassing means for urging the clamping mechanism into a closed position.

15. A docking mechanism according to claim 14, in which the docking mechanism includes electrical connector biassing means, weaker than said clamping mechanism biassing means, for urging the electrical connector into engagement with the sensor of a cartridge in the docking mechanism.

16. A docking mechanism according to claim 14, in which the clamping mechanism and electrical connector biassing means form part of the actuating mechanism.

17. A docking mechanism according to claim 16, in which the electrical connector is mounted on a further carrier member movable relative to cartridge in the docking mechanism to bring the electrical connector into and out of engagement with the sensor.

18. A docking mechanism according to claim 17, in which the electrical connector biasing means acts on said further carrier member.

19. A docking mechanism according to claim 17, in which the further carrier member comprises a printed circuit board which includes interface circuitry for matching the sensor to operating circuitry.

20. A docking mechanism according to claim 9, in which the actuation means is operable to close the clamping mechanism before bringing the electrical connector into engagement with a sensor.

21. A docking mechanism according claim 2, in which the carrier member and electrical connector are arranged in an opposed relationship so that a cartridge received in the docking mechanism is interposed between the carrier member and the electrical connector.

22. A docking mechanism according to claim 2, in which the co-operating surface is so arranged as to engage the cartridge to retain the latter in position in the docking mechanism.

23. A docking mechanism according to claim 22, in which the co-operating surface comprises a formation, for example a rib or groove, which is fixed relative to the docking mechanism and which receives an edge portion of a cartridge.

24. A docking mechanism according to claim 23, in which said formation forms part of, or is attached to, a frame of the docking mechanism.

25. A docking mechanism according to claim 1, in which the electrical connector is one of two such connectors, each for connecting a respective electrode of the sensor to the circuitry.

26. A docking mechanism according to claim, 1, in which the or each electrical connector comprises a spring loaded pin.

27. Apparatus for analysing samples comprising a fluid, the apparatus comprising a cartridge having an electrically operated sensor for analysing the sample, a docking mechanism according to claim 1, for releasably receiving the cartridge, sample delivery means for delivering the sample, via the docking mechanism to the cartridge and electrical circuitry for operating the sensor.

28. Apparatus according to claim 27, in which the cartridge contains a flow cell for bringing the sample into contact with the sensor.

29. Apparatus according to claim 27, in which the sensor comprises an electrical-mechanical transducer.

* * * * *